United States Patent [19]
York, Jr.

[11] Patent Number: 4,717,725
[45] Date of Patent: * Jan. 5, 1988

[54] OPHTHALMIC WOUND HEALING WITH ALDOSE REDUCTASE INHIBITORS

[75] Inventor: Billie M. York, Jr., Fort Worth, Tex.

[73] Assignee: Alcon Laboratories, Inc., Fort Worth, Tex.

[*] Notice: The portion of the term of this patent subsequent to Mar. 13, 2001 has been disclaimed.

[21] Appl. No.: 816,870

[22] Filed: Jan. 7, 1986

Related U.S. Application Data

[63] Continuation-in-part of Ser. No. 599,283, Apr. 11, 1984, Pat. No. 4,600,717.

[51] Int. Cl.$^4$ .............................................. A61K 31/44
[52] U.S. Cl. .................................... 514/278; 514/376; 514/389; 514/409; 514/866
[58] Field of Search ............... 514/278, 376, 389, 409, 514/866

[56] References Cited

U.S. PATENT DOCUMENTS

| | | | |
|---|---|---|---|
| 3,821,383 | 6/1974 | Sestanj et al. | 424/258 |
| 4,117,230 | 9/1978 | Sarges | 548/309 |
| 4,130,714 | 12/1978 | Sarges | 548/309 |
| 4,181,728 | 1/1980 | Sarges et al. | 424/273 R |
| 4,436,745 | 3/1984 | York, Jr. | 424/273 R |
| 4,438,272 | 3/1984 | York, Jr. | 548/308 |
| 4,537,892 | 8/1985 | York, Jr. | 514/278 |
| 4,600,717 | 7/1986 | York | 514/278 |

*Primary Examiner*—Leonard Schenkman
*Attorney, Agent, or Firm*—James Arno; Gregg C. Brown; Robert L. Price

[57] ABSTRACT

Method of promoting healing of ocular wounds comprising the topical application of an aldose reductase inhibitor; compositions comprising such inhibitors are also disclosed.

8 Claims, No Drawings

OPHTHALMIC WOUND HEALING WITH ALDOSE REDUCTASE INHIBITORS

CROSS-REFERENCE TO RELATED APPLICATION

This application is a continuation-in-part of U.S. application Ser. No. 599,283, filed Apr. 11, 1984 now U.S. Pat. No. 4,600,717, dated July 15, 1986.

BACKGROUND OF THE INVENTION

This invention relates to methods and compositions useful in promoting ocular wound healing. Specifically, this invention relates to compositions comprising an aldose reductase inhibitor; and methods of treatment comprising administering these compositions when it is desired to promote ocular wound healing.

While applicant is bound by no theory, it appears that the mechanism of wound healing is related to the mechanism of aldose reductase inhibition and the role of that event in mediating the effects of diabetes. Thus, the method and compositions of the present invention are directed to diabetic individuals. In diabetes there is a condition of high glucose or hyperglycemia. When glucose levels are high, an enzyme called aldose reductase converts glucose to sorbitol at the expense of NADPH. The accumulation of a polyol, such as sorbitol within cells causes pathological changes to those cells and in the tissues comprising those cell. These sickened cells or tissues are not capable of effecting a normal physiological response associated with wound healing (e.g., effecting normal cell migration and division). The corneal epithelium and endothelium of the eye contains aldose reductase. In diabetics the rate of cornea wound healing is retarded significantly. On occasion, vision impairing and painful corneal ulceration and scaring results from retarded or abnormal corneal wound healing in the diabetic. The aldose reductase inhibitors inhibit the enzyme aldose reductase within the cornea and thereby promote wound healing in the diabetic. These aldose reductase inhibitors can be applied topically to the eye or systemically to the diabetic to promote wound healing when indicated. While the present disclosure is premised on the above reasonings, the instant compositions and methods of the present invention are not restricted to the diabetic syndrome.

DETAILED DESCRIPTION OF THE INVENTION

Aldose reductase inhibitors which are particularly suitable for the method of the present invention and pharmaceutical compositions comprising these inhibitors are disclosed in the following copending, commonly assigned U.S. patent applications: U.S. patent application Ser. No. 532,168 filed Sept. 14, 1983, now U.S. Pat. No. 4,537,892, and U.S. patent application Ser. No. 368,630 filed Apr. 15, 1982, now U.S. Pat. No. 4,436,745, similarly, attention is directed to the following U.S. Pat. Nos. 4,438,272; 3,821,383; 4,117,230; 4,130,714; and 4,181,728. To the extent these applications and patents disclose aldose reductase inhibitors which are useful in the practice of the present invention, they are incorporated herein by reference.

A particularly preferred group of aldose reductase inhibitors which are useful in the invention are the spirocyclic aromatic imides of the following general formula:

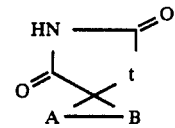

and the pharmaceutically acceptable metal salts and in cases, where basic aromatic nitrogens are in the A, and/or B rings, the pharmaceutically acceptable organic and inorganic acid salts thereof, wherein A and B are aromatic or heterocyclic rings connected through two adjacent positions to a central cycloalkyl ring, the A and B rings being selected from the group consisting of those of the formula:

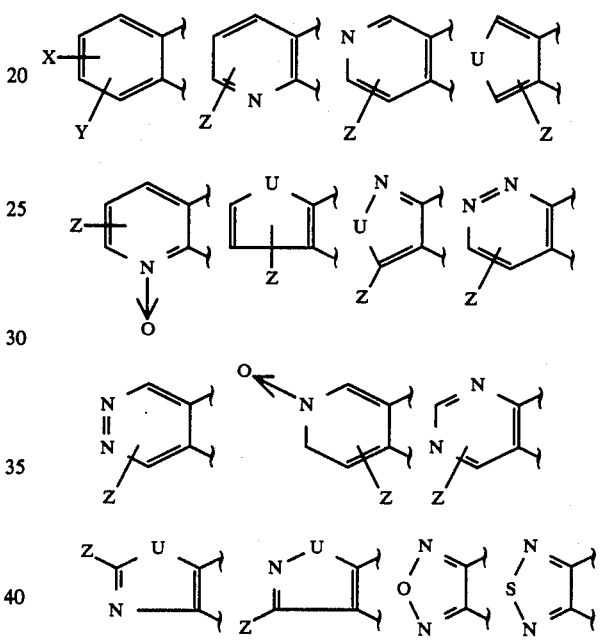

and wherein

U is selected from the group consisting of O, S, N—$R^1$;

X is selected from the group consisting of H, F, lower alkyl sulfide (e.g., —S—$CH_3$), lower alkylsulfinyl (e.g., —S(O)$CH_3$);

Y is selected from the group consisting of H, —OH, and

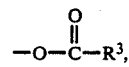

F, Cl, lower alkyl, lower alkoxy, lower alkylsulfide (e.g., —S—$CH_3$), lower alkyl-sulfinyl (e.g., —S-(O)—$CH_3$), lower alkylsulfonyl (e.g., —$SO_2CH_3$), —$CF_3$, —S—$CF_3$, —$SO_2CF_3$, CO—N($R^1$)—$R^2$, lower alkyl alcohol (e.g., —$CH_2$—OH), lower alkyl ether (e.g., —$CH_2OCH_3$), nitro, lower alkyl sulfide lower alkyl (e.g., —$CH_2S$—$CH_3$), lower alkylamine (e.g., —$CH_2NH_2$), lower alkyl esters (e.g., —$CH_2$—O—$COCH_3$), carboxylic acids and lower alkyl esters (e.g., —$COOR^3$), lower alkyl carboxylic acids and esters (e.g., —CH($CH_3$)—$COOR^1$), and lower cycloalkyl (e.g., cyclopropyl);

$R^1$ and $R^2$ are selected from the group consisting of H and lower alkyl (preferably methyl or ethyl);

$R^3$ is lower alkyl (preferably methyl or ethyl);

Z is selected from the group consisting of H, lower alkyl (preferably methyl), and halogen (fluoro, chloro, bromo, iodo); and t is selected from the group consisting of NH, O, S, and $CHR^1$.

In a more preferred embodiment, the spiro-cyclic aromatic imides of the present invention are of the following general formula:

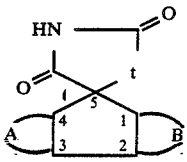

I-A.

wherein A, B, U, X, Y, $R^1$, $R^2$, $R^3$, Z, and t are as described above. In more preferred embodiments, the cycloalkyl groups have 4 to 7 carbon atoms and lower alkyl groups have 1 to 6 carbon atoms. In an especially preferred embodiment, Ring A is selected from the foregoing group and Ring B is selected from the group consisting of the following:

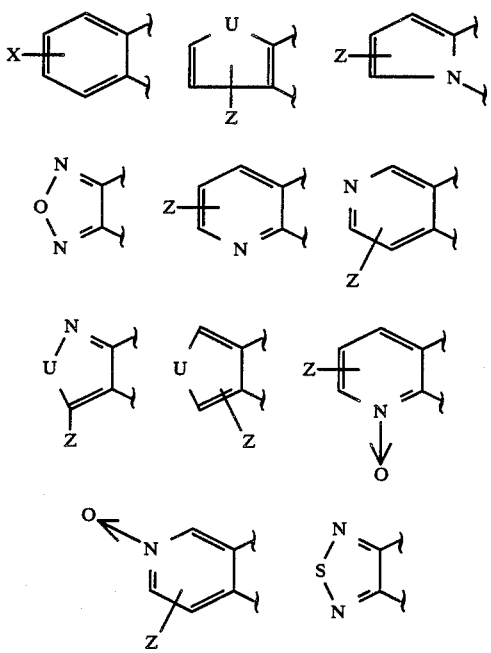

where X, U, and Z are described above. In the compounds of Formulae I and I-A, Rings A and B are attached to the central five-membered ring at positions 1,2 and 3,4.

The compounds of the present invention have important geometric and chemical similarities. These similarities include a planar, rigid tricyclic fluorene or fluorene-like aromatic ring system spiro-coupled to a five-membered imide (or cyclic secondary amide) ring such as succinimide, hydantoin, thiazolidinedione or oxazolidinedione. These spirocyclic derivatives of the various tricycles each contain a polarizable and hydrogen-bondable secondary amide, also called imide, radical (—CO—NH—CO—).

In those instances where, according to general Formulae I and I-A, A does not equal B, the spiro carbon is chiral. Activity of any such racemic mixture may be attributable to only one isomer. Resolution, or direct synthesis, of the enantiomers, as is known in the art, is recognized as a method to isolate or prepare the active or the more active enantiomer. It is also recognized that certain patterns of substitution on A and/or B according to Formulae I and I-A may create asymmetry, and the resulting diastereomeric mixtures may be separated by chromatography or solvent recrystallizations, as is known and practiced in the art. For example, if A has a methylsulfoxyl substituent and A is different from B, then there are at least two chiral centers: the spiro carbon and the sulfoxide sulfur. Physical separation of this diastereomeric mixture by chromatography or other methods practiced in the art will yield two racemic mixtures, each containing a pair of enantiomers. Stereospecific oxidation of a methylsulfide on A to yield a methylsulfoxide (e.g., via sodium metaperiodate and albumin) when A is different than B (according to Formula I) will yield a diastereomeric mixture, which then can be separated by conventional physical methods known in the art, such as liquid chromatography or differential solvent solubility, to yield the purified diastereomers which are themselves purified optical isomers. Reduction of the two optically active sulfoxide diastereomers will yield the optically active pair of enantiomers or mirror image isomers.

Of special interest in this invention are typical and preferred specie of Formula I such as these racemic mixtures: spiro-(6-fluoro-4H-indeno[1,2-b]thiophen-4,4'-imidazolidine)-2',5'-dione; spiro-(7-fluoro-9H-pyrrolo[1,2-a]indol-9,4'-imidazolidine)-2',4'-dione; spiro-(2-fluoro-9H-fluoren-9,4'-imidazolidine)-2',5'-dione; spiro-(6-fluoro-8H-indeno[2,1-b]thiophen-8,4'-imidazolidine)-2',5'-dione; spiro-(2-fluoro-9H-fluoren-9,3'-succinimide); spiro-(2-fluoro-9H-fluoren-9,5'-thiazolidine)-2',4'-dione; spiro-(7-fluoro-9H-indeno[2,1-c]pyridin-9,4'-imidazolidine)-2',5'-dione; spiro-(7-fluoro-5H-indeno[1,2-b]pyridin-5,4'-imidazolidine)-2',5'-dione; spiro-(7-fluoro-5H-indeno[1,2-c]pyridin-5,4'-imidazolidine)-2',5'-dione; spiro-(7-fluoro-9H-indeno[2,1-b]pyridin-5,4'-imidazolidine)-2',5'-dione; spiro-(7-fluoro-5H-indeno[1,2-c]pyridin-5,5'-thiazolidine)-2',4'-dione; spiro-(7-fluoro-5H-indeno[1,2-b]pyridin-5,5'-thiazolidine)-2',4'-dione; spiro-(7-fluoro-9H-indeno[2,1-c]pyridin-9,5'-thiazolidine)-2',4'-dione; spiro-(7-fluoro-9H-[2,1-b]pyridin-9,5'-thiazolidine)-2',4'-dione; spiro-(7-fluoro-5H-indeno[1,2-b]pyridin-5,3'-succinimide; spiro-(7-chloro-5H-[1,2-b]pyridin-5,5'-thiazolidine)-2',4'-dione; spiro-(7-chloro-5H-[1,2-b]pyridin-5,5'-oxazolidine)-2',4'-dione; spiro-(6-fluoro-4H-indeno[1,2-b]thiophen-4,5'-thiazolidine)-2',4'-dione; spiro-(6-chloro-8H-indeno[2,1-b]thiophen-8,5'-thiazolidine)-2',4'-dione; spiro-(2-fluoro,7-methylthiol-9H-fluoren-9-,5'-thiazolidine)-2',4'-dione.

Also of special interest in this invention are these achiral or nonracemic compounds: spiro-(2,7-difluoro-9H-fluoren-9,4'-imidazolidine)-2',5'-dione; spiro-(2,7-difluoro-9H-fluoren-9,5'-thiazolidine)-2',4'-dione; spiro-(2,7-difluoro-9H-fluoren-9,3'-succinimide); spiro-(2,7-difluoro-9H-fluoren-9,5'-oxazolidine)-2',4'-dione. All the aforementioned compounds are highly potent as regards their aldose reductase inhibitory activities. All of the aforementioned preferred compounds as in Formula I may be formulated as the base salts thereof with pharmacologically acceptable cations (e.g., sodium salt). Alternatively, several preferred examples such as spiro-(7-fluoro-5H-indeno[1,2-b]pyridin-5,5'-thiazolidine)-2',4'-dione and related examples which contain a basic nitrogen in ring(s) A and/or B according to Formula I can be formulated as the acid salt with pharmacologically acceptable strong acids (e.g., hydrochloride salt).

The spiro-tricyclic-thiazolidinedione, -imidazolidinedione, -oxazolidinedione and -succinimide compounds of the present invention are weak acids. In addition, several examples, as cited in Example XIX, are carboxylic acid derivatives and/or aromatic azines (i.e., contain a basic nitrogen(s) in the aromatic tricycle) and/or contain an alkylamine substituent. Therefore, these compounds are amenable to preparation as base salts and in some cases, where basic amines are present, acid salts. Several examples contain both an acidic spiro functionality and carboxylic acid functionality. These cases can be prepared as mono- or di-basic salts.

The chemical bases which are used as reagents to prepare the aforementioned pharmaceutically acceptable base salts are those which form nontoxic (pharmaceutically acceptable) salts with the various herein described acidic spiro-imidazolidinedione, -thiazolidinedione, -oxazolidinedione and -succinimdie derivatives such as spiro-(7-fluoro-5-H-indeno[1,2-b]pyridine-5,4'-imidazolidine)-2',5'-dione, for example. Similarly, herein described carboxylic acid containing derivatives, such as spiro-(2-carboxy-9H-fluoren-9,5'-thiazolidine)-2',4'-dione, can be prepared as nontoxic salts. These nontoxic base salts are of a nature not to be considered clinically toxic over a wide therapeutic dose range. Examples of such cations include those of sodium, potassium, calcium, magnesium, etc. These pharmacologically acceptable nontoxic salts can be prepared by treating the aforementioned acidic specie, e.g., spiro-thiazolidinedione, with aqueous metallic hydroxide solution, and then evaporating the resulting solution, preferably at reduced pressure, to dryness. Alternatively, where indicated, the base salts can be prepared by mixing a lower alkanolic solution (e.g., ethanol) of the acidic compound with a desired alkali metal alkoxide (e.g., sodium ethoxide) in a lower alkanolic solution, and evaporating the solution to dryness in the same manner as before. In any case stoichiometric quantities of reagents must be employed in order to ensure completeness of reaction and maximum production of yields with respect to the final base salt product.

Acid salts of spiro-tricyclic azine derivatives, e.g., spiro-(7-fluoro-5H-indeno[1,2-b]pyridine-5,5'-thiazolidine)-2',4'-dione, can be prepared with nontoxic pharmacologically acceptable acids, e.g., hydrochloric acid and sulfuric acid. Examples of such anions of said acid salts include those of hydrogensulfate, sulfate, chloride, etc. These pharmacologically acceptable nontoxic acid salts can be prepared by treating the aforementioned basic specie, e.g., spiro-azafluorene derivative, with an acidic aqueous solution of the desired acid. After the basic species is solubilized in the acid, the solution is evaporated to dryness, preferably with reduced pressure. In this case, stoichiometric quantities of acid are preferred. Alternatively, in some cases the acid salt may be precipitated or recrystallized from strong acid solution (e.g., 5% hydrochloric acid). The salt then is collected by filtration and dried.

Methods for synthesis of aldose reductase inhibitors for use in the invention are known and are described for example in applicant's U.S. Pat. No. 4,537,892. The following are specific compounds prepared by the method of applicant's prior patent.

EXAMPLE I

9-Hydroxy-9H-fluorene-9-carboxylic acid methyl ester (1)

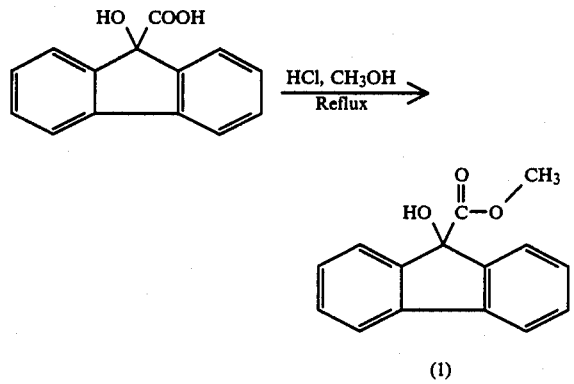

9-Hydroxy-9H-fluorene-9-carboxylic acid (Aldrich Chemical, Inc.) (20.0 g, 88.4 mmol) was added to 100 mL methanol saturated with hydrogen chloride and mixture was stirred at reflux for 4 h. The crystalline material obtained on cooling was collected by filtration and washed with cold 1:1 ethyl acetate/hexane to provide after drying (1), 15.8 g (74%).

Spiro-(9H-fluorene-9,5'-oxazolidine)-2',4'-dione (2)

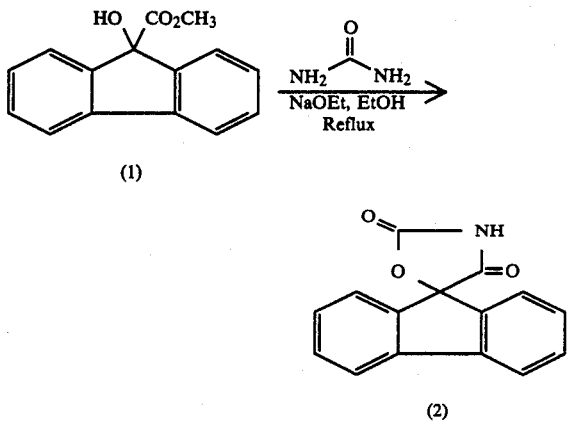

To a stirred solution of sodium (190 mg, 8.26 mmol) in 20 mL absolute ethanol was added urea (500 mg, 8.26 mmol) and 9-hydroxy-9H-fluorene-9-carboxylic acid methyl ester (1) (2.00 g, 8.26 mmol). The mixture was stirred at reflux under nitrogen for 15 h. After cooling to room temperature, the reaction mixture was poured into 100 mL water and acidified with 2N aqueous hydrochloric acid to precipitate the product which was collected by filtration, washed with water, and dried to provide 1.5 g crude (2). Recrystallization from ethyl acetate gave 260 mg (12%): m.p. 225°-257° C. A second crop, 620 mg (30%), was obtained by evaporation of the mother liquor followed by recrystallization from ethyl acetate/hexane. M/e+·251. For the preparation of oxazolidinediones from α-hydroxy esters using urea and sodium ethoxide, see: Stoughton, *J. Am. Chem. Soc.* (1941) 63, 2376.

EXAMPLE II

2-Fluoro-9H-fluorene-9-carboxylic acid (3)

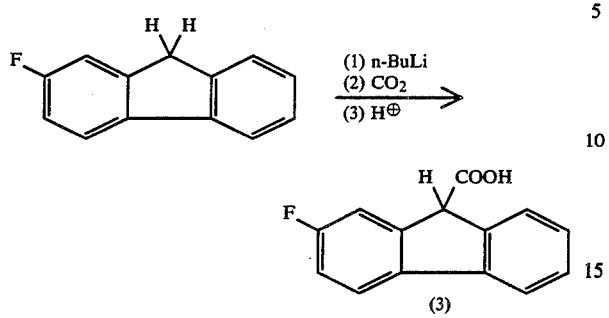

Under nitrogen atmosphere, n-butyllithium (1.25 eq, 0.170 mL, 65 mL of a 2.6M hexane solution) was added dropwise over 30 min. to a stirred 0.5° C. solution of 2-fluorofluorene (prepared according to U.S. application Ser. Nos. 368,630 and 368,631) (25.0 g, 0.136 mmol) in 500 mL dry THF. After an additional 35 min. a flow of dry carbon dioxide gas into the solution was commenced and continued for 15 min. at 0°–15° C. and 45 min. at room temperature. 2N aqueous hydrochloric acid (200 mL) was added, and the mixture was transferred to a separatory funnel. The aqueous layer was separated and extracted 1×100 mL ethyl acetate. The combined organic phases were washed 1×100 mL brine, dried (MgSO4), and evaporated to leave a dark residue which was triturated with 250 mL hexane to leave 16.6 g crude acid. Recrystallation from acetonitrile gave 10.2 g of the acid (3). A second crop of 2.0 g was obtained from the concentrated filtrate. Chromatography of the filtrate and the concentrated hexane extract on silica gel using 10–50% ethyl acetate/hexane provided another 2.8 g. Total yield: 15.0 g (48%).

2-Fluoro-9H-fluorene-9-carboxylic acid methyl ester (4)

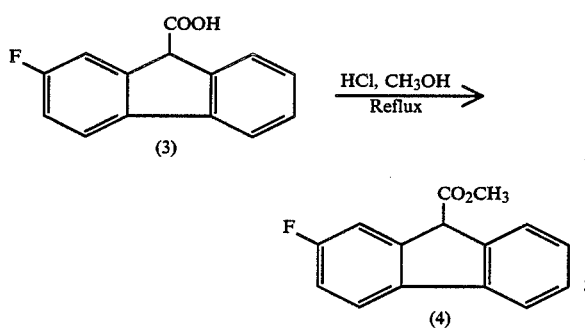

Acetyl chloride (33 mL) was added dropwise to a stirred, ice-cold solution of 2-fluoro-9H-fluorene-9-carboxylic acid (3) (16.7 g, 73.2 mmol) in 200 mL methanol and the solution was then refluxed for 4 h. Solvent removal left the crude product which was recrystallized from methanol to provide (4), 14.1 g (79%): m.p. 90°–92° C. (from hexane). For the preparation of 9H-fluorene-9-carboxylic acid from fluorene using phenyllithium and esterification using methanolic hydrogen chloride see: Bavin, *Anal. Chem.* (1960) 32, 554.

2-Fluoro-9-hydroxy-9H-fluorene-9-carboxylic acid methyl ester (5)

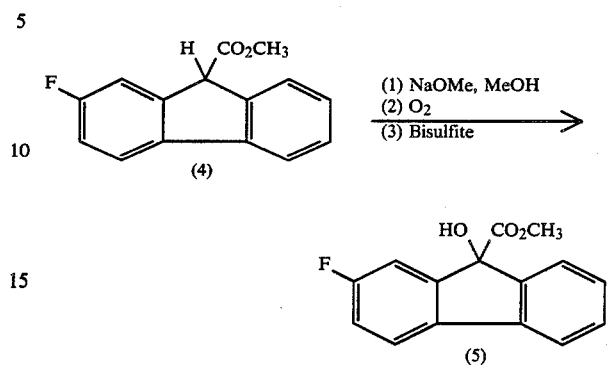

To a stirred solution of sodium (1.25 eq, 22.3 mmol, 510 mg) in 100 mL methanol was added 2-fluoro-9H-fluorene-9-carboxylic acid methyl ester (4) (4.33 g, 17.9 mmol). After 15 min. a flow of dry oxygen into the solution was commenced and continued for 1 h. Some of a solution of sodium bisulfite (24.5 g) in 300 mL water was added until the reaction became cloudy. The mixture was then poured into the remaining bisulfite solution. After cooling in ice, the solid that separated was collected by filtration, washed well with water, and dried to provide (5), 4.05 g (88%).

Spiro-(2-fluoro-9H-fluorene-9,5'-oxazolidine)-2',4'-dione (6)

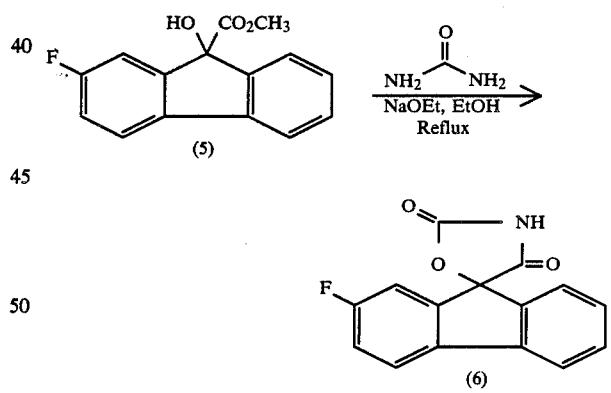

To a stirred solution of sodium (1.03 eq, 130 mg) in 13 mL absolute ethanol was added 2-fluoro-9-hydroxy-9H-fluorene-9-carboxylic acid methyl ester (5) (1.42 g, 5.5 mmol) and urea (5.5 mmol, 330 mg). The mixture was then refluxed 15 h. After cooling to room temperature, the mixture was poured into 65 mL water and acidified with 2N aqueous hydrochloric acid. The yellow solid that separated was collected, washed with water, and dried to give 1.19 g crude material. Chromatography on silica gel using 1–100% methanol/chloroform gave pure (6), 580 mg (39%). m/e+ 269.

EXAMPLE III

9-Chloro-9H-fluorene-9-carboxylic acid methyl ester (7)

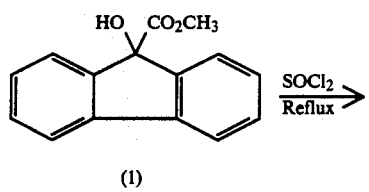

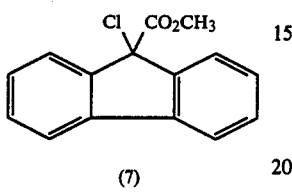

A mixture of 9-hydroxy-9H-fluorene-9-carboxylic acid methyl ester (1) (5.00 g, 20.8 mmol) and 50 mL thionyl chloride was heated at reflux for 3 h. The thionyl chloride was removed on the rotavapor to leave a solid residue which was redissolved in 50 mL benzene and then evaporated to remove traces of thionyl chloride. The resulting material was recrystallized from acetic acid to give (7), 3.23 g (60%): m.p. 111°–114° C. An additional 960 mg (18%) of product was obtained by chromatography of the reduced filtrate on silica gel using 10% ethyl acetate/hexane.

Spiro-[9H-fluorene-9,5'-(2'-amino-4'-thiazolone)] (8)

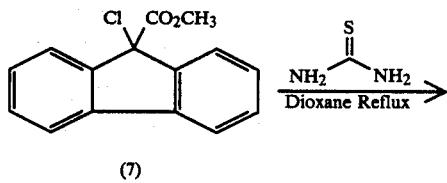

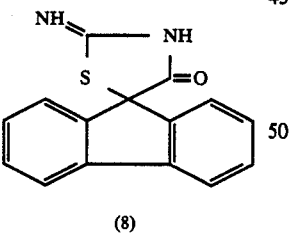

A mixture of 9-chloro-9H-fluorene-9-carboxylic acid methyl ester (7) (4.21 g, 16.3 mmol) and thiourea (1.24 g, 16.3 mmol) in 150 mL dioxane was heated at reflux for 10 h. After cooling to room temperature, the fine white solid present was collected by filtration and washed with dioxane providing (8), 1.31 g (30%). The gummy residue which remained in the flask was chromatographed on silica gel using 10–20% methanol/chloroform to give another 220 mg (5%) of (7): m.p. 320°–322° C. (dec). For the preparation of 2-imino-4-thiazolidinones from α-halo acid halides using thiourea in dioxane, see: Skinner, *J. Org. Chem.* (1961) 26, 1450.

Spiro-(9H-fluorene-9,5'-thiazolidine)-2',4'-dione (9)

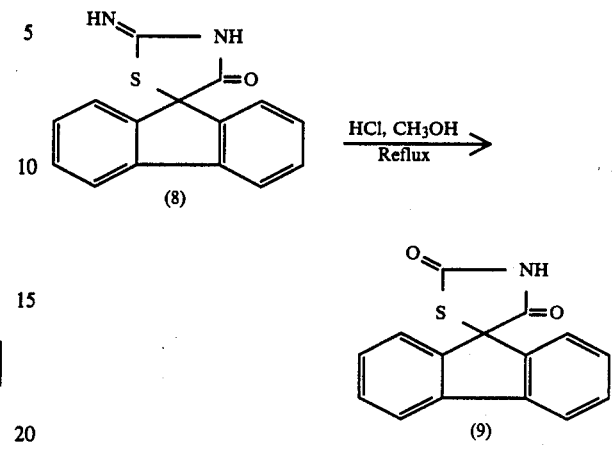

A mixture of spiro-[9H-fluorene-9,5'-(2'-amino-4'-thiazolone)] (8) (1.19 g, 4.47 mmol), 24 mL methanol, and 24 mL concentrated hydrochloric acid was refluxed 4 h. The reaction mixture was cooled in ice and the white precipitate was collected by filtration, washed with water, and dried to provide 640 mg crude (9). Recrystallization from acetonitrile gave 490 mg (41%): m.p. 253°–255° C. A second crop of 80 mg (7%) was obtained from the mother liquor. Calc. %C 67.40, %H 3.39; %N 5.24: meas. %C 67.46, %H 3.34, N 5.32. For the hydrolysis of 2-amino-4-thiazolones to thiazolidinediones using methanolic hydrogen chloride, see: Koltai, *Tetrahedron* (1973) 29, 2781.

EXAMPLE IV

9-Chloro-2-fluoro-9H-fluorene-9-carboxylic acid methyl ester (10)

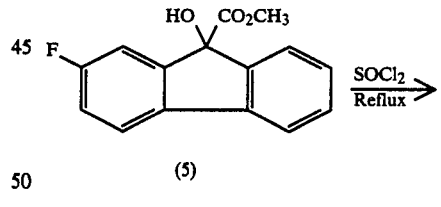

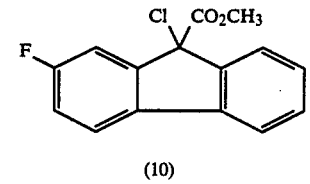

A mixture of 2-fluoro-9-hydroxy-9H-fluorene-9-carboxylic acid methyl ester (5) (4.00 g, 15.5 mmol) and 50 mL thionyl chloride was refluxed 3 h. After the thionyl chloride was removed on the rotavapor, the material was redissolved in 50 mL benzene and the benzene then evaporated to remove trace thionyl chloride. The crude product, 4.3 g (100%), was used without further purification.

Spiro-[2-9H-fluorene-9,5'-(2'-amino-4'-thiazolone)] (11)

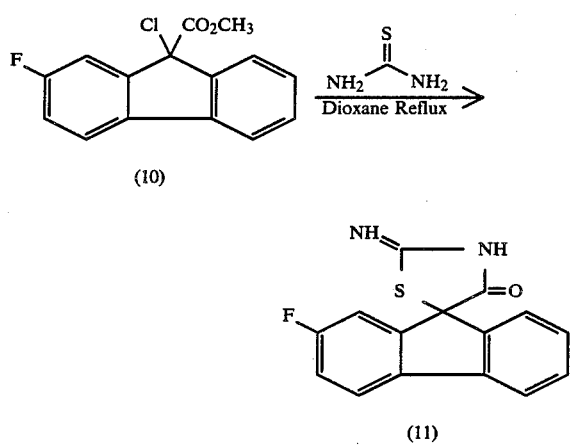

A mixture of 9-chloro-2-fluoro-9H-fluorene-9-carboxylic acid methyl ester (10) (4.31 g, 15.6 mmol) and thiourea (1.1 eq, 17.2 mmol, 1.31 g) in 140 mL dioxane was refluxed for 10 h. After cooling to room temperature, the fine white precipitate was collected by filtration and washed with water providing (11), 1.28 g (29%). An additional 1.3 g (29%) of (11) was obtained by chromatography of the reduced filtrate on silica gel using 5–50% methanol/chloroform.

Spiro-(2-fluoro-9H-fluorene-9,5'-thiazolidine)-2',4'-dione (12)

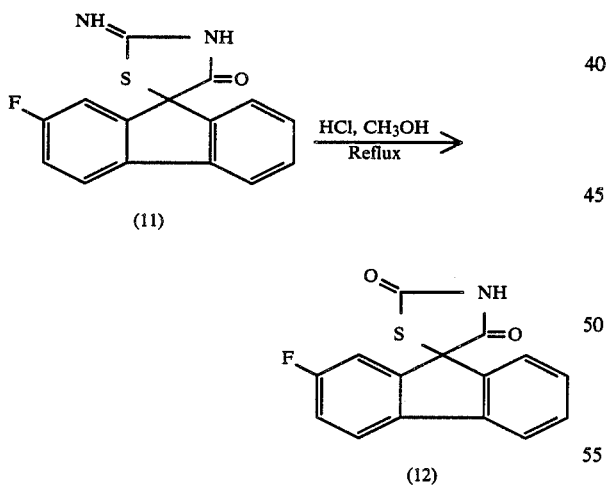

A mixture of spiro-[2-fluoro-9H-fluorene-9,5'-(2'-amino-4'-thiazolone)] (11) (1.85 g, 6.51 mmol), 35 mL methanol, and 35 mL concentrated hydrochloric acid was heated at reflux for 6 h. After cooling to room temperature, the white precipitate was collected by filtration and washed with water to provide 1.22 g of crude (12). Recrystallization from ethanol provided three crops totaling 870 mg (47%): m.p. 272°–276° C. (dec). m/e+·285.

EXAMPLE V 2,7-Difluoro-9H-fluorene-9-carboxylic acid (13)

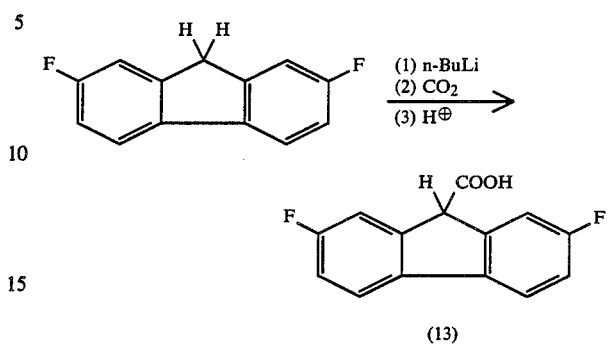

To a stirred, room temperature solution of 2,7-difluorofluorene (prepared according to U.S. application Ser. Nos. 368,630 and 368,631) (10.0 g, 49.5 mmol in 75 mL dry diethyl ether under a nitrogen atmosphere was added over 15 min n-butyllithium (1.25 eq, 61.9 mmol, 24 mL of a 2.6M hexane solution). The solution was refluxed 30 min., cooled to room temperature, and then quickly poured onto an ether slurry of a large excess of powdered dry ice. After the dry ice evaporated, the mixture was transferred to a separatory funnel along with 100 mL 2N aqueous hydrochloric acid and 50 mL ethyl acetate. After shaking well, the organic layer was separated and evaporated to dryness. The residue was extracted 2×100 mL warm (50° C.) 2% aqueous sodium hydroxide and then the extract was acidified with concentrated hydrochloric acid to precipitate the impure acid which was collected by filtration and washed with water. This material was dissolved in 50% ethyl acetate/hexane and passed through a 50 mm×7 silica gel column using the same solvent to remove highly colored, baseline impurities and to provide (13) sufficiently pure to be used in the next step, 7.91 g (65%): m.p. 128°–130° C. (from benzene).

2,7-Difluoro-9H-fluorene-9-carboxylic acid methyl ester (14)

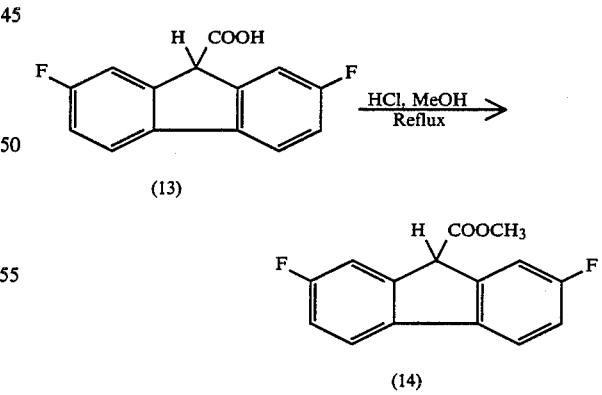

Acetyl chloride (13 mL) was added dropwise to a stirred, ice-cold solution of 2,7-difluoro-9H-fluorene-9-carboxylic acid (14) (6.90 g, 28 mmol) in 77 mL methanol. The mixture was then heated at reflux for 4 h. The product which crystallized upon cooling in ice was collected by filtration and washed with cold methanol to provide (14), 5.15 g (71%): m.p. 161°–163° C. (from toluene).

2,7-Difluoro-9-hydroxy-9H-fluorene-9-carboxylic acid methyl ester (15)

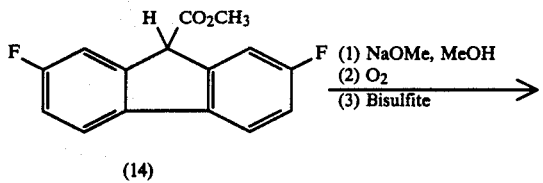

(14)

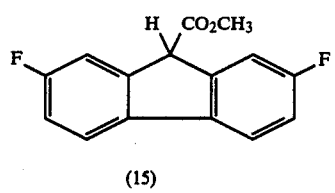

(15)

2,7-Difluoro-9H-fluorene-9-carboxylic acid methyl ester (14) (4.73 g, 18.2 mmol) was added to a solution of sodium (1.25 eq, 22.7 mmol, 520 mg) in 100 mL methanol. After 15 min., a flow of dry oxygen into the solution as commenced and continued for 1 h. Some of a solution of 24.5 g sodium bisulfite in 800 mL water was added until the mixture turned cloudy and then the whole was poured into the remaining bisulfite solution. The solid was collected by filtration, washed with water, and dried to provide (15), 4.68 g (93%): m.p. 174°-176° C. (from benzene).

9-Chloro-2,7-difluoro-9H-fluorene-9-carboxylic acid methyl ester (16)

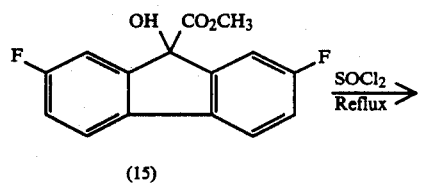

(15)

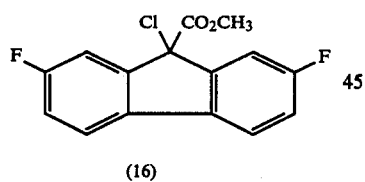

(16)

A mixture of 2,7-difluoro-9-hydroxy-9H-fluorene-9-carboxylic acid methyl ester (15) (3.63 g, 13.1 mmol) and 50 mL thionyl chloride was heated at reflux for 4 h. The reaction mixture was then diluted with 300 mL benzene and evaporated to leave (16), 3.7 g (96%), which was used in the next step without further purification: m.p. 140°-142° C. (from acetonitrile).

Spiro-[2,7-difluoro-9H-fluorene-9,5'-(2'-amino-4'-thiazolone)] (17)

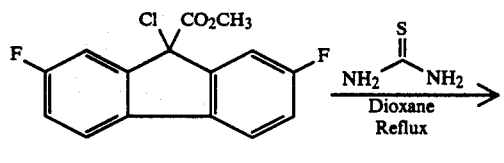

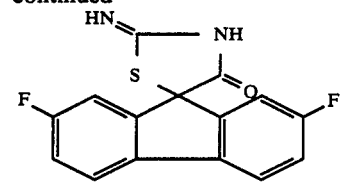

(17)

A mixture of 9-chloro-2,7-difluoro-9H-fluorene-9-carboxylic acid methyl ester (16) (3.56 g, 12.1 mmol) and thiourea (1.1 eq, 13.3 mmol, 1.01 g) in 110 mL dry dioxane was heated at reflux for 12 h. After cooling to room temperature and in ice, the white precipitate was collected by filtration, washed with dioxane, and dried to provide (17), 490 mg (13%). The concentrated filtrate and the gummy residue which remained in the flask were individually chromatographed on silica gel using 5-20% methanol/chloroform to provide another 1.00 g (27%) product: m.p. >300° C.

Spiro-(2,7-difluoro-9H-fluorene-9,5'-thiazolidine)-2',4'-dione (18)

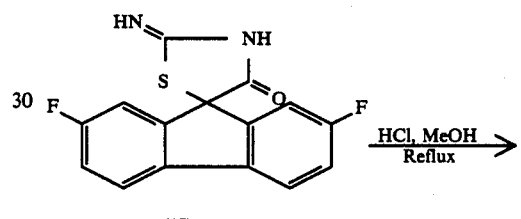

(17)

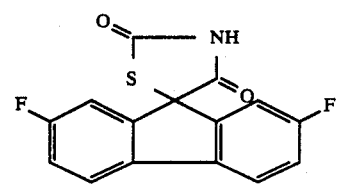

(18)

A mixture of spiro-[2,7-difluoro-9H-fluorene-(2'-amino-4'-thiazolone)] (17) (1.17 g, 3.87 mmol), 21 mL methanol, and 21 mL concentrated hydrochloric acid was refluxed for 6 h. The reaction mixture was cooled in ice and the off-white precipitate was collected by filtration, washed with water, and dried to provide 900 mg crude (18). This material was chromatographed on silica gel using 5-10% methanol/chloroform to yield pure (18), 530 mg (45%): m.p. 260°-263° C. (dec). Calc. %C 59.40, %H 2.33, %N 4.62: meas. %C 59.47, %H 2.42, %N 4.64.

EXAMPLE VI

Spiro-(9H-fluoren-9,3'-succinimide) (20)

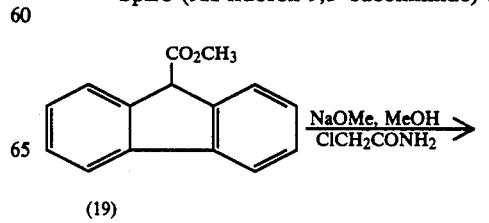

(19)

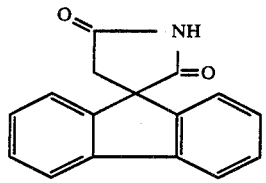

(20)

9H-fluoren-9-carboxylic acid methyl ester (19), which was prepared by refluxing 9H-fluoren-9-carboxylic acid (Aldrich Chemical, Inc.) in HCl/MeOH, (10.0 g, 44.6 mmol) was added to a solution of sodium (1.2 eq, 53.5 mmol, 1.23 g) in 100 mL methanol. After 15 min., 2-chloroacetamide (1.1 eq, 49.1 mmol, 4.59 g) was added and the mixture was allowed to stir at room temperature under nitrogen for two (2) days. The reaction mixture was poured into 400 mL of cold 2.5% w/v aqueous sodium hydroxide and the insoluble material was removed by filtration. The filtrate was chilled and acidified with concentrated hydrochloric acid to precipitate the spiro-succinimide which was collected and air dried to provide 6.7 g (60%). Recrystallization from methanol gave purified (20), 4.28 g (39%). m.p. 237°–239° C. Calc. %C 77.09, %H 4.45, %N 5.62: meas. %C 77.17, %H 4.55, %N 5.58.

EXAMPLE VII

Spiro-(2-fluoro-9H-fluoren-9,3'-succinimide) (21)

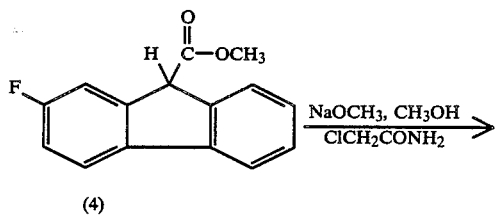

(4)

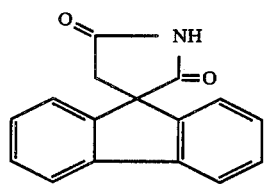

(21)

The spiro-succinimide (21), m.p. 248°–250° C., was prepared analogous to Example VI except from (4) in 25% yield. Calc. %C 71.90, %H 3.77, %N 5.24: meas. %C 71.97, %H 3.87, %N 5.33.

EXAMPLE VIII

5H-Indeno[1,2-b]pyridine-5-carboxylic acid methyl ester (22)

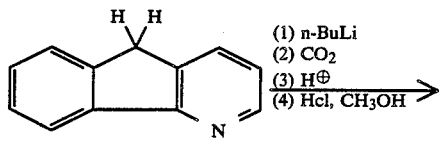

(Available Aldrich)

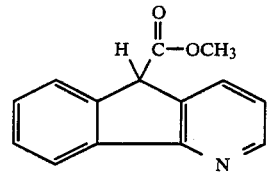

(22)

Under a nitrogen atmosphere, n-butyllithium (1.2 eq, 105 mmol, 65 mL of a 2.6M hexane solution) was added dropwise over a 30 min. period to a stirred 0°–5° C. solution of 4-azafluorene (14.65 g, 87.6 mmol) in 150 mL dry tetrahydrofuran (dried and distilled from LAH). After 1 h 20 min. the reaction mixture was poured into an ether slurry containing a large excess of dry ice. Solvents were allowed to evaporate overnight. The residue was suspended in 300 mL methanol, chilled and 60 mL acetyl chloride was added dropwise over 45 min. and the mixture stirred for 22 h at room temperature. Purification by chromatography (30% ethyl acetate/hexanes on silica gel) and solvent evaporation yields 16.3 g (83%) of (22).

5-Hydroxy-5H-indeno[1,2-b]pyridine-5-carboxylic acid methyl ester (23)

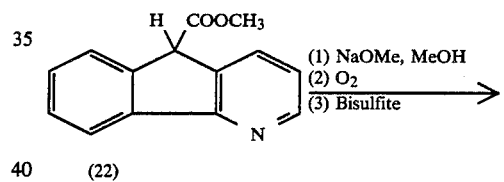

(22)

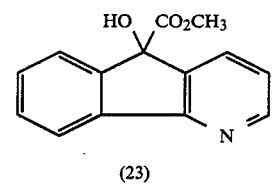

(23)

To a stirred solution of sodium (1.1 eq, 60.1 mmol, 1.38 g) in 150 mL dry methanol was added a solution of 5-hydroxy-5H-indeno[1,2-b]pyridine-5-carboxylic acid methyl ester (22) (12.3 g, 54.6 mmol) in 50 mL dry methanol. The solution was cooled in ice and, after 15 min., a flow of dry oxygen was begun and continued for 1 h. Then the reaction mixture was poured into a solution of 12 g sodium bisulfite in 200 mL water. After 30 min. the mixture was evaporated to dryness. The resulting solid was triturated with 2X 100 mL acetone and filtered. The remaining inorganic salts were removed by filtration. The filtrate was evaporated to yield 24.2 g wet pink solid of (23). Drying in vacuo over phosphorus pentaoxide yielded 12.5 g crude (23). Recrystallization from ethyl acetate yielded two crops 8.06 g (61%) and 2.54 g (19%) of (23).

5-Chloro-5H-indeno[1,2-b]pyridine-5-carboxylic acid methyl ester (24)

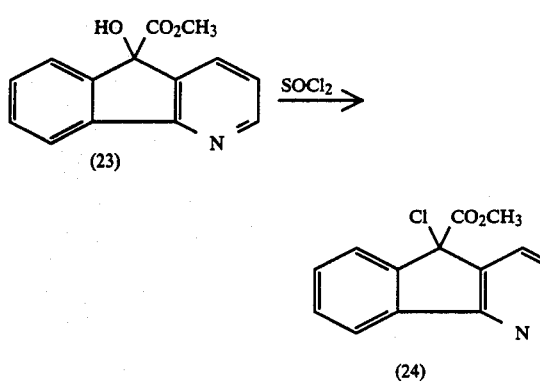

A mixture of 5-hydroxy-5H-indeno[1,2-b]pyridine-5-carboxylic acid methyl ester (23) (8.06 g, 33.4 mmol) in 200 mL thionyl chloride was heated at reflux for 4 h. The thionyl chloride was removed on the rotavapor to leave a residue which was partitioned between water and chloroform and neutralized with saturated sodium bicarbonate. After further extractions with chloroform the combined chloroform extracts were dried over magnesium sulfate and evaporated to yield 7.87 g (91%) of (24).

Spiro-[5H-indeno[1,2-b]pyridine-5,5'-(2'-amino-4'-thiazolone)] (25)

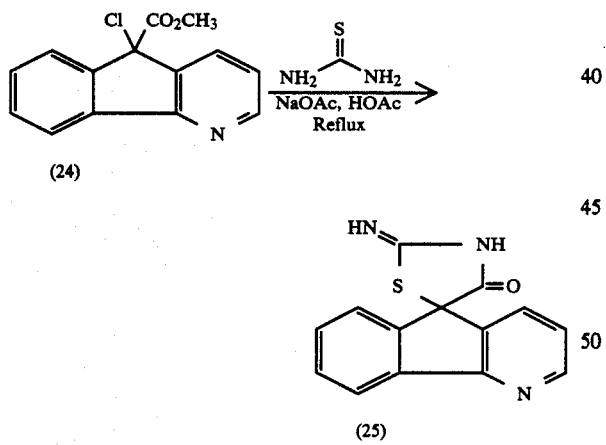

A mixture of 5-chloro-5H-indeno[1,2-b]pyridine-5-carboxylic acid methyl ester (24) (7.87 g, 30.4 mmol), thiourea (1.2 eq, 36.4 mmol, 2.77 g) and sodium acetate (1.1 eq, 33.4 mmol, 2.74 g) in 140 mL glacial acetic acid was refluxed for 40 min. Then 100 mL water was added and the pH was adjusted to 6.7 with hydrochloric acid. The aqueous portion was decanted from the precipitate, followed by additional 50 mL water wash. The dried residue was treated with ethyl acetate and the resulting crystalline solid was collected by filtration and dried to yield 1.81 g (32%) of (25).

Spiro-(5H-indeno[1,2-b]pyridine-5,5'-thiazolidine)-2',4'-dione (26)

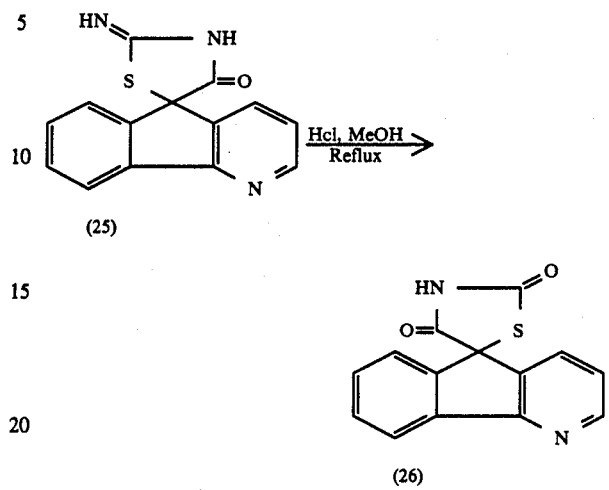

A mixture of spiro-[5H-indeno[1,2-b]pyridine-5,5'-(2'-amino-4'-thiazolone)] (25) (1.00 g, 3.74 mmol) was stirred at reflux in a solution of 100 mL methanol and concentrated hydrochloric acid (1:1) for 2 h. The mixture was then concentrated to approximately 10 mL with heat and reduced pressure, chilled on ice and neutralized with sodium hydroxide solution. The resulting precipitate was collected by filtration and washed with water. Purification of the dried precipitate by chromatography (silica gel using 2.5–7% methanol/chloroform) yielded a product after solvent evaporation, 400 mg. Recrystallization of the residue from ethanol yielded crystalline (26). m/e+·268. IR strong bands at 1700 and 1745 cm$^{-1}$.

EXAMPLE IX

Spiro-(5H-indeno[1,2-b]pyridine-5,3'-succinimide) (27)

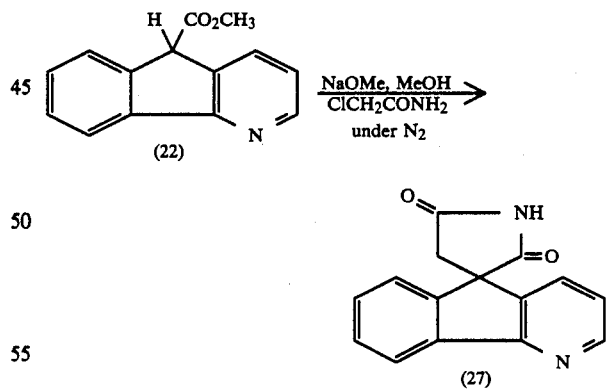

The ester (22) (4.00 g, 17.8 mmol) was added all at once to a stirred, room temperature solution of sodium methoxide in methanol (sodium metal, 1.2 eq, 21.3 mmol, 490 mg and 40 mL dry methanol). After 15 min., chloroacetamide (1.1 eq, 19.5 mmol, 1.83 g) was added and the mixture was left to stir at room temperature under nitrogen. After two days the reaction mixture was poured into 100 mL 1N sodium hydroxide, cooled in ice and the pH was adjusted with concentrated hydrochloric acid to pH 7. The precipitated solid was collected by filtration and washed with cold water. The dried solid (2.02 g) was recrystallized from ethyl acetate with charcoal treatment to yield 1.03 g (23%) crystalline (27). m.p. 245°-246° C. Calc. %C 71.99, %H 4.03, %N 11.20: meas. %C 71.85, %H 4.14, %N 11.17.

EXAMPLE X

5H-Indeno[1,2-b]pyridin-5-one (28)

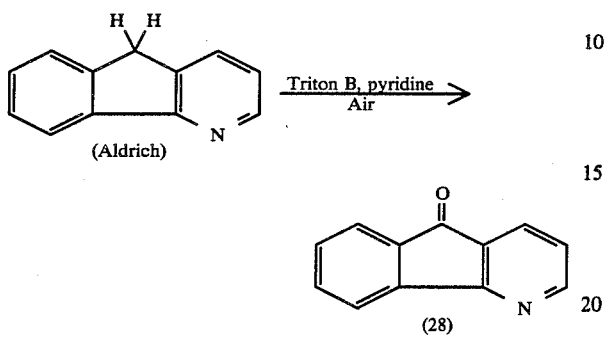

See general oxidation method of Sprinzak, J. Am. Chem. Soc., 80 (1958) 5449. 4-Azafluorene (5.0 g, 30 mmol) was dissolved in 50 mL anhydrous pyridine containing in solution 2 mL Triton B solution (prepared by evaporating 5 mL of 40% Triton B in methanol (Aldrich Chemical, Inc.) and 5 mL pyridine with heat and reduced pressure followed by q.s. to 10 mL with pyridine). Then air was continuously bubbled through the solution with stirring. An addition of 2 mL Triton B solution was made twice more at two-hour intervals. After six hours the reaction mixture was evaporated to dryness. The residue was triturated in 30 mL water and extracted four times with ethyl acetate (total volume 200 mL). The combined ethyl acetate extracts were dried over anhydrous sodium sulfate. After filtration and evaporation, the residue was chromatographed (silica gel and chloroform) to yield after evaporation of the solvent 4.5 g (83%) of (28). m.p. 132°-136° C. (reported 142° C.).

Spiro-(5H-Indeno[1,2-b]pyridine-5,4'-imidazolidine)-2',5'-dione (29)

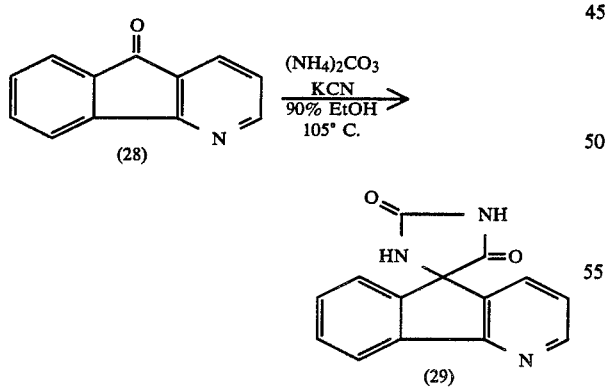

5H-Indeno[1,2-b]pyridine-5-one (4.0 g, 22 mmol) was mixed with potassium cyanide (1.6 g, 24 mmol) and ammonium carbonate (5.3 g, 55 mmol) in 90% ethanol (75 mL) in a pressure reactor and heated at 105° C. for 40 hr. The mixture was poured into 300 mL of water, acidified with conc. HCl (pH 1), and filtered. The filtrate was neutralized and the solid which formed collected by filtration, washed with water, and dried to yield 4.5 g. This solid was crystallized from ethyl acetate to yield 3.2 g of product. (This material was no longer soluble in ethyl acetate after the first crystallization). m/e+·251.

EXAMPLE XI

Spiro-(7-nitro-indeno[1,2-b]pyridin-5,4'-imidazolidine)-2',5'-dione (30)

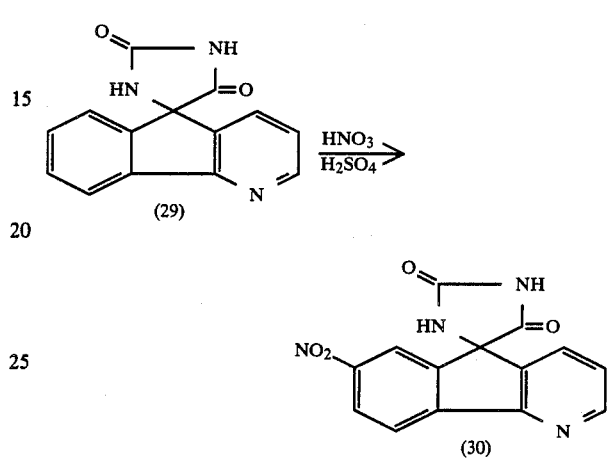

Spiro-(indeno[1,2-b]pyridine-5,4'-imidazolidine)-2',5'-dione (29) (1.0 g, 4 mmol) was added to cold concentrated sulfuric acid (10 mL) and stirred in an ice bath as concentrated nitric acid was added dropwise over about 10 min. The mixture was allowed to warm to room temperature and stirred overnight; the resulting solution was poured onto ice and the solution neutralized with concentrated aqueous sodium hydroxide. The solid which formed was collected by filtration, washed with a small volume of water, and dried. The product was dissolved in warm water (30 mL) by the addition of sodium hydroxide solution, treated with Norite decoloring charcoal, filtered through a celite bed and the bed washed with a small volume of warm dilute base. The combined filtrate and wash were neutralized with hydrochloric acid to yield a solid which was collected by filtration, washed with water and dried to yield 0.76 g of (30). Calc. %C 56.76, %H 2.72, %N 18.91: meas. %C 56.59, %H 2.83, %N 18.87. m/e+·296.

EXAMPLE XII

Spiro-(7-bromo-indeno[1,2-b]pyridine-5,4'-imidazolidine)-2',5'-dione (31)

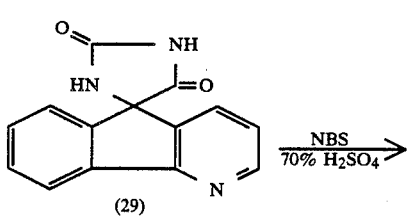

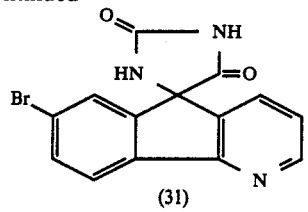

Spiro-(indeno[1,2-b]pyridin-5,4'-imidazolidine)-2',5'-dione (29) (1.0 g, 4 mmol) was dissolved in cold 70% sulfuric acid (50 mL). The solution was heated to 50° C., and N-bromosuccinimide (0.78 g, 4.3 mmol) was added in small portions with stirring. After stirring at 50° C. for 2 h, the reaction was poured onto ice, and the solution was neutralized with concentrated aqueous sodium hydroxide. The solid which formed was collected by filtration and washed with water. The sample was dissolved in 30 mL of warm water by addition of aqueous sodium hydroxide then treated with Norite, filtered through a celite bed and washed with warm dilute base, and the combined filtrate and wash were acidified with hydrochloric acid (to pH 6). The solid was collected by filtration, washed with water, and dried to yield 0.88 g of (31). m/e+·329.

EXAMPLE XIII

4H-indeno[1,2-b]thiophen-4-one (35)

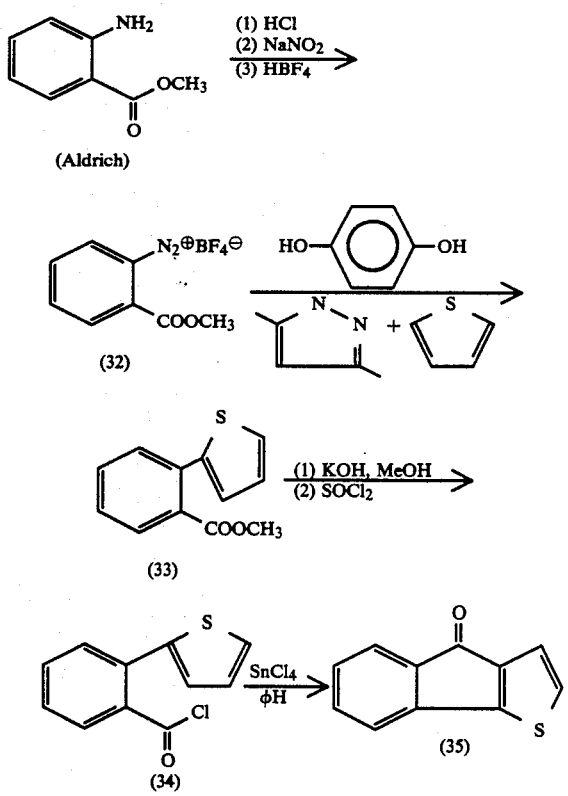

To methyl anthranilate (90.0 g, 77 mL, 595 mmol, 1.0 eq) was added hydrochloric acid (120 mL of conc., 1450 mmol, 2.4 eq diluted with 100 mL distilled water). The resulting mixture of solid and liquid was heated to reflux with stirring while protected from light. The hot clear solution was cooled to 5° C. whereupon a solid precipitated. To this stirred mixture was added sodium nitrite solution (41.09 g, 596 mmol, 1.0 eq in 90 mL distilled water) at a rate to maintain the reaction temperature below 5° C. After 1.5 h fluoroboric acid (95 g, 48% in water) was added rapidly and the resulting suspension was stirred for an additional 30 min. at −10° to 0° C. The suspended solid was collected by filtration, washed with 100 mL cold water, 120 mL cold methanol and 500 mL ether. The resulting pink solid was dried in vacuo over concentrated sulfuric acid to yield 39.5 g of (32) as a pink solid (m.p. 93°-98° C. with decomposition, reported 102° C. with decomposition *Org. Reactions* 5, 219).

To a diazo salt (32) (39.5 g, 158 mmol, 1.0 eq) in thiophene (75 mL) stirred suspension was dropwise added during 1 h a solution consisting of 3,5-dimethylpyrazole (15.80 g, 164 mmol, 1.04 eq) and hydroquinone (1.91 g, 17 mmol, 0.11 eq) in 125 mL thiophene at 0° C. After 2.5 h additional stirring at 0°-5° C. the reaction was stirred overnight at ambient temperature (see *J. Org. Chem.*, 46 (1981) 3960). Evaporation with heat and reduced pressure yielded a brown semisolid. Column chromatography (silica gel, 1:9 to 1:4 ethyl ether/petroleum ether) yields 19.4 g. Distillation (bp 141°-160° C., 4 mmHg) yields 15.1 g of (33).

To 15.1 g of (33) was added methanolic potassium hydroxide (12.8 g KOH in 200 mL methanol) and the reaction mixture was refluxed for 4 h whereupon potassium hydroxide (2.5 g) was added. After 5 h total refluxing, the starting material (33) was completely hydrolyzed (silica gel, 40% Pot ether/ether). To the cooled mixture was added 250 mL water and the diluted mixture was extracted with 250 mL ethyl ether. The ether extract was back extracted with 150 mL 10% KOH. The combined aqueous fractions were cooled and acidified with concentrated hydrochloric acid to pH 2. The acidified slurry was then extracted with diethyl ether (3×200 mL), the ether extracts washed with brine (150 mL) then dried with anhydrous magnesium sulfate. After filtration and evaporation, 23.7 g tan solid resulted. m.p. 80° C. (reported m.p. 93°-94° C., *J. Med. Chem.*, 9 (1966) 551). To the acid (13.7 g, 69.2 mmol, 1.0 eq) was added thionyl chloride (25.3 mL, 213 mmol, 3.1 eq) and the mixture was refluxed for 2 h. After cooling the reaction mixture was evaporated with reduced pressure and heat with 3×100 mL benzene additions to result in 15 g of (34) as a dark oil.

Under nitrogen, a stannic chloride solution (SnCl4, 9.1 g, 4.1 mL, 1.25 eq in 40 mL benzene) was added over 20 min. to a benzene (100 mL) solution of the acid chloride (34) (15 g, 69.2 mmol) at 0°-4° C. with mechanical stirring. After a total of 30 min. the reaction mixture was poured into 200 cc ice containing 100 mL 1N hydrochloric acid. (See *J. Org. Chem.*, 35 (1970) 872). Ethyl acetate extractions (600 mL) of the aqueous mixture yielded a dark organic extract. Washing the organic extract with 100 mL 100% sodium hydroxide, 100 mL water (2X) yielded an orange ethyl acetate extract which was dried over anhydrous magnesium sulfate. Filtration and evaporation yielded a dark residue. Column chromatography (silica gel, 1:9 ethyl ether/petroleum ether) yields a purified 4.5 g sample of orange (35). m.p. 99.5°-101.5° C. from hexane. (lit. 101° C., *J. Org. Chem.* 35 (1970) 872). Calc. %C 70.94, %H 3.25, %S 17.22: meas. %C 70.98, %H 3.33, %S 17.16.

Spiro-(4H-indeno[1,2-b]thiophen-4,4'-imidazolidine)-2',5'-dione (36)

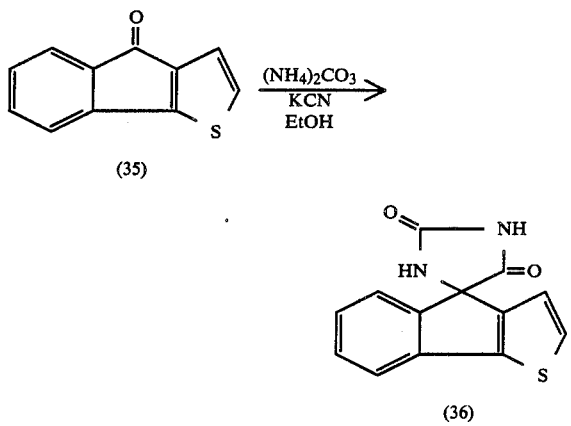

To a glass-lined, high-pressure steel reaction vessel was added ketone (35) (373 mg, 2 mmol), potassium cyanide (406 mg, 5 mmol), ammonium carbonate (577 mg, 6 mmol) and ethanol (15 mL). The sealed vessel was heated at 110° C. for 24 h. The dark reaction mixture was poured into water and acidified with concentrated hydrochloric acid to pH 1. The resulting dark solid was collected by filtration and resolubilized in 10% sodium hydroxide (30 mL), treated with charcoal and filtered. The filtrate was acidified with concentrated hydrochloric acid. The resulting precipitate was collected by filtration and dried. The solid was dissolved in dimethylformamide, treated with Darco G-60 and filtered through a Celite pad. Dilution with water (3X volume) resulted in a precipitate which was collected by filtration. The collected solid was dissolved in 10% sodium hydroxide (3 mL), filtered, and the filtrate was acidified with conc. hydrochloric acid, the white precipitate collected by filtration, washed with water and dried at 105° C. to yield 110 mg of (36). m.p. 336°-8° C. Calc. %C 60.92, %H 3.15, %N 10.96: meas. %C 60.83, %H 3.22, %N 10.97.

EXAMPLE XIV

8H-Indeno[2,1-b]thiophen-8-one (38)

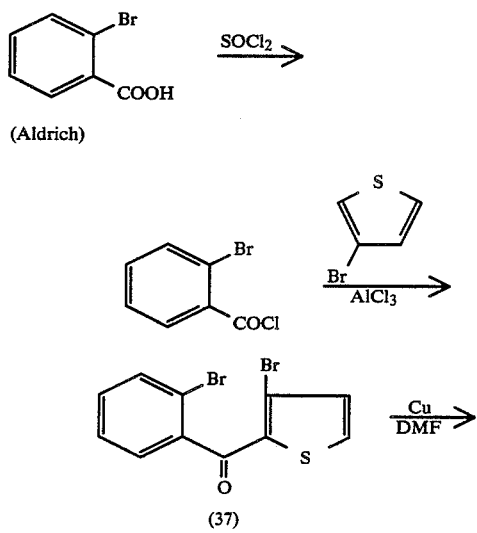

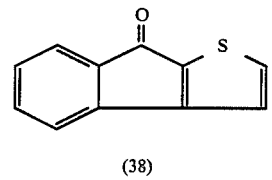

Thionyl chloride (60.3 g, 37 mL, 500 mmol, 3.6 eq) was added at 25° C. to o-bromobenzoic acid (Aldrich Chemical, Inc.) (28.1 g, 140 mmol, 1.0 eq). After addition the reaction mixture was heated to 80° C. for 13 h. Evaporation with heat and reduced pressure partially reduced the volume. Then under nitrogen atmosphere 100 mL methylene chloride followed by 3-bromothiophene (Aldrich Chemical, Inc.) (22.8 g, 13.1 mL, 140 mmol, 1.0 eq) in 100 mL methylene chloride were added to acyl chloride intermediate. Then aluminum trichloride (23.9 g, 179 mmol, 1.3 eq) was added in small portions to the reaction mixture at 0° C. After addition, the reaction mixture was allowed to slowly reach room temperature. After 17 h the reaction was quenched by the slow addition of 150 mL 2N hydrochloric acid. Water (2×150 mL) and brine (100 mL) washing, drying over anhydrous magnesium sulfate, filtration and evaporation of the filtrate in vacuo yielded approximately 50 g of an oil of (37) which solidified in the freezer. IR 1645 cm$^{-1}$ for diaryl ketone.

Diaryl ketone (37) (44 g, 480 mmol, 4 eq) and activated copper (prepared from aqueous copper sulfate, zinc dust, 5% hydrochloric acid) (30 g, 480 mmol, 4 eq) in 200 mL dimethylformamide were refluxed for 6.5 h. After the cooling the reaction mixture was filtered and 150 mL water added. The filtrate was extracted with ethyl ether (5×150 mL). The combined ether extracts were washed with 150 mL 1N hydrochloric acid, 150 mL water and 150 mL brine. Then the ether solution was dried over anhydrous magnesium sulfate, filtered and evaporated to yield a solid, 18.6 g (79%). Recrystallization from hexane yielded purified (38) m.p. 111°-112° C. Calc. %C 70.97, %H 3.25, %S 17.22: meas. %C 70.71, %H 3.26, %S 17.12.

Spiro-(8H-indeno[2,1-b]thiophen-8,4'-imidazolidine)-2',5'-dione (39)

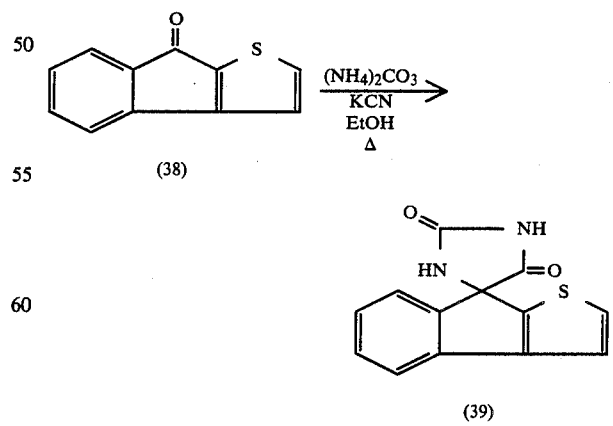

To a glass-lined, high-pressure steel reaction vessel was added ketone (38) (931.2 mg, 5 mmol), potassium cyanide (1.01 g, 12.5 mmol), ammonium carbonate (1.45 g, 18 mmol) and 25 mL ethanol. The sealed vessel was heated at 115°–120° C. for 20 h. The work-up procedure was very similar to that for spiro-hydantoin (36) of Example XIII. The purified product (39), 200 mg, gave m/e+·256. Calc. %C 60.92, %H 3.15, %N 10.96: meas. %C 60.88, %H 3.22, %H 10.79.

EXAMPLE XV

Spiro-(9H-pyrrolol[1,2-a]indol-9,4′-imidazolidine)-2′,4′-dione (41)

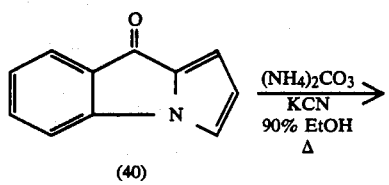

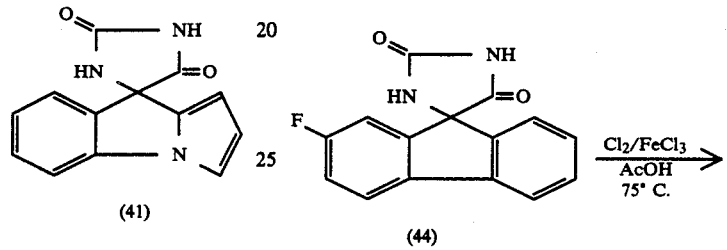

9H-Pyrrolol[1,2-a]indole-9-one (40) was prepared exactly according to Josey and Jenner, *J. Org. Chem.*, 27 (1962) 2466. The ketone (40) (2.5 g, 15 mmol), potassium cyanide (2.44 g, 37.5 mmol), ammonium carbonate (4.85 g, 45 mmol) and 50 mL 90% ethanol were added with mixing to a 125 cc stainless steel pressure reaction vessel. The sealed vessel was heated to 115°–118°0 C. for 48 h. The work-up was as in Example XIII in the work-up of (36). The collected and dried sample, 650 mg of (41), gave decomposition at >290° C. Calc. %C 65.26, %H 3.79, %N 17.56: meas. %C 65.16, %H 4.00, %N 17.59.

EXAMPLE XVI

Spiro-(9H-indeno[2,1-c]pyridin-9,4′-imidazolidine]-2″,5′-dione (43)

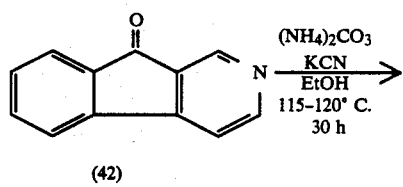

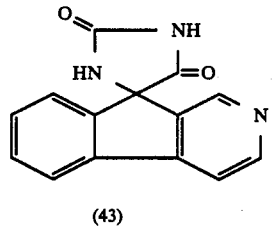

2-Azafluoren-9-one (42) was prepared from 3-mesitoyl-4-phenyl-pyridine exactly according to Fuson and Miller, *J. Am. Chem. Soc.*, 79 (1957) 3477. m.p. 152°–153° C. (reported 155.5°–156.5° C. by Fuson and Miller, ibid). The ketone (42) (0.5 g, 2.8 mmol), potassium cyanide (0.2 g, 3.1% mmol), ammonium carbonate (1.0 g, 11 mmol) and 10 mL absolute ethanol were added with mixing to a 40 cc stainless steel pressure reactor. The sealed vessel was heated at 115°–120° C. for 30 h. The cooled reaction mixture was poured into 75 mL water, acidified with concentrated hydrochloric acid, filtered, the filtrate was made basic with 10% sodium hydroxide and filtered. The filtrate was neutralized with hydrochloric acid, the precipitate collected, washed with cold water and dried to yield 0.11 g of (43). m/e+·251.

EXAMPLE XVII

Spiro-(2-chloro-7-fluoro-9H-fluoren-9,4′-imidazolidine)-2′,5′-dione (45)

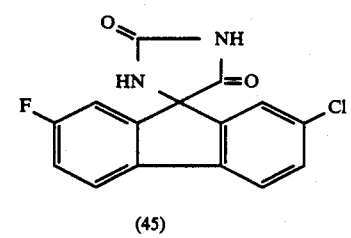

The spiro-hydantoin (44), spiro-(2-fluoro-9H-fluoren-9,4′-imidazolidine)-2′,5′-dione, was prepared exactly according to U.S. application Ser. Nos. 368,630 and 368,631. A mixture of (44) (5.36 g, 20 mmol), ferric chloride (0.25 g), glacial acetic acid solution of chlorine gas (5 g Cl₂ in 25 mL HOAc) and 200 mL glacial acetic acid were heated at 75° C. overnight. The cooled reaction mixture was poured into 200 mL water, stirred and the solid was collected by filtration. After water washes, the solid product was dried with 50° C. heat in vacuo to yield 2.3 g of (45). Calc. %C 59.52, %H 2.66, %N 9.25: meas. %C 59.35, %H 2.77, %N 9.26.

EXAMPLE XVIII 7-fluoro-5H-indeno[1,2-b]pyridine (50)

The procedure used for the preparation of 5-fluoro-1-indanone is that of Olivier and Marechal (*E. Bull. Soc. Chim. Fr.* (1973) 3092–3095) with modifications. The conversion of the ketone to 7-fluoro-5H-indeno[1,2-b]pyridine followed the general procedure described by Parcell and Hauck (*J. Org. Chem.* (1963) 28, 3468–3473) for the preparation of 5H-indeno[1,2-b]pyridine from 1-indanone.

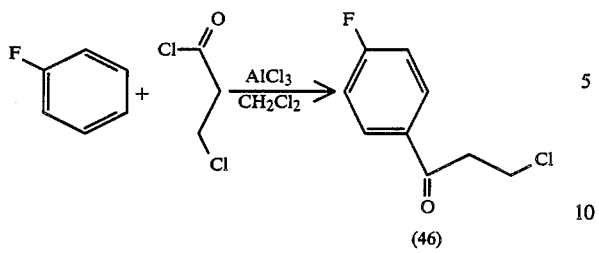

(46)

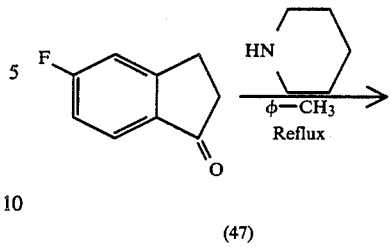

(47)

Aluminum chloride (350 g, 2.62 mol) was covered with 650 mL methylene chloride and, while stirring under nitrogen, a solution of 3-chloropropionyl chloride (400 g, 3.15 mol, 300 mL) in 250 mL methylene chloride was added over 80 min. After 15 min., a solution of fluorobenzene (256 g, 2.66 mol, 250 mL) in 250 mL methylene chloride was added over 1 h 35 min. The reaction mixture was stirred, under nitrogen, at room temperature overnight (ca 18 h). The mixture was then poured onto 2.5 kg ice and transferred to a 4 L separatory funnel. After shaking well, the organic layer was removed and the aqueous portion was extracted with 2×50 mL methylene chloride. The combined organic extracts were washed with 3×200 mL saturated aqueous sodium bicarbonate and 1×200 mL brine, dried (MgSO4), and evaporated to leave an oil which crystallized on cooling. Recrystallization from 2 L hexane gave 325 g (67%). The filtrate was concentrated to 500 mL and cooled to provide another 42 g (9%) of product (46).

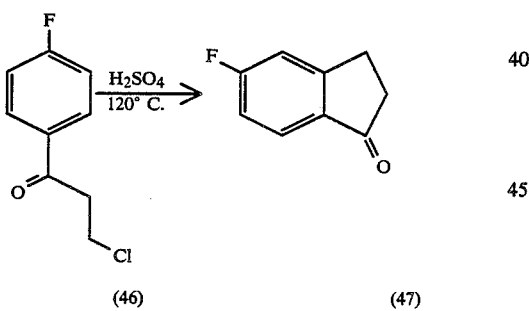

(46)    (47)

3-Chloro-1-(4-fluorophenyl)propanone (46) (366 g, 1.97 mol) and 2.2 L concentrated sulfuric acid were combined in a 5 L flask equipped with a mechanical stirrer and heated over a period of 80 min. to 120° C. and then maintained at that temperature for 30 min. Hydrogen chloride evolution began at about 80° C. The reaction mixture was then cooled to 20° C., poured onto 5 kg of ice in a 22 L flask equipped with a bottom drain and a mechanical stirrer, and extracted with 6×1 L chloroform. The combined extracts were washed with 2×1 L saturated aqueous sodium bicarbonate and 1×1 L brine, dried (MgSO4), and concentrated to leave a dark oil. Distillation gave the ketone, (47) 97.9 g (33%), bp 61°-66° c./0.15-0.2 mm, discolored by some dark material which was carried over during the process.

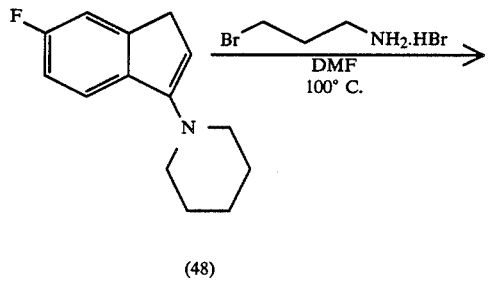

(48)

A solution of 5-fluoro-1-indanone (47) (20.2 g, 0.135 mol), p-toluene-sulfonic acid monohydrate (0.015 eq, 390 mg), and piperidine (1.1 eq, 0.148 mol, 15 mL) in 300 mL toluene was refluxed under a Dean-Stark trap for 30 h. The reaction mixture was concentrated and distilled to provide the enamine, (48) 8.6 g (29%); bp 95°-100° C./1.5 mm.

(48)

(49)

A solution of the enamine (8.6 g, 40 mmol) in 10 mL dry DMF was added all at once to a stirred solution of bromopropylamine hydrobromide (1.0 eq, 8.67 g) in 15 mL DMF. The stirred mixture was heated to 100° C. under nitrogen and then kept at that temperature for 4 h. The reaction mixture was poured into 60 mL cold 2N aqueous hydrochloric acid and extracted with 2×50 mL ethyl ether to remove any non-basic material. The aqueous solution was then covered with 50 mL ether, chilled, and basified using concentrated sodium hydroxide. After separating the organic layer, the aqueous portion was extracted with 2×50 mL ether and the combined extracts were washed with 1×50 mL brine, dried (MgSO4), and concentrated to leave 7.8 g of a dark oil. Distillation provided the tetrahydropyridine, 3.46 g (46%); bp 83°-86° C./0.15 mm.

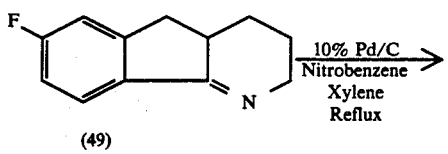

(49)

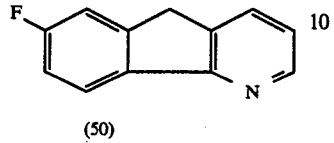

(50)

A mixture of the tetrahydropyridine (49) (3.19 g, 16.9 mmol), 10 mL xylene, 10 mL nitrobenzene, and 350 mg 10% palladium on carbon was refluxed for 4 h under a Dean-Stark trap under nitrogen. The reaction mixture was then cooled to room temperature and filtered through Celite, washing with ethyl acetate. The filtrate was extracted with 3×20 mL 2N aqueous hydrochloric acid and then the combined extracts were washed with 2×25 mL ethyl ether to remove non-basic material. Basification using solid potassium carbonate resulted in the precipitation of a dark green solid that was collected by filtration and washed well with water. This material 2.3 g (75%), was judged sufficiently pure by NMR to use in the next step. The material can further be purified by chromatography on silica gel using 30% ethyl acetate/hexane to give a yellow solid of (50) mp 80°-84° C.

EXAMPLE XIX

Following the foregoing text of preparations and examples, from readily available starting materials, the following spiro-derivatives of the present invention are prepared by analogy. All structural permutations occasioned by the substitution patterns and the values of U and Z on the following tricyclic structures are fully contemplated and intended as evidenced by the table entries.

UNSUBSTITUTED PARENT STRUCTURES FOR COMPOUNDS 1-328:A-D

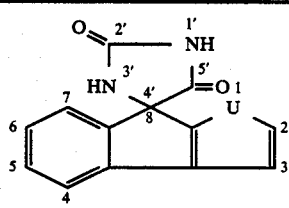

A

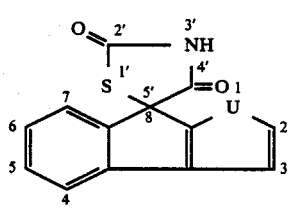

B

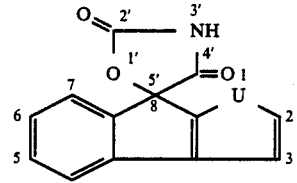

C

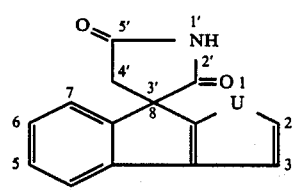

D

| Compound No. | Substitution | U |
|---|---|---|
| 1-4: A-D | 7-F | NH, N—CH$_3$, S, O |
| 5-8: A-D | 6-F | NH, N—CH$_3$, S, O |
| 9-12: A-D | 5-F | NH, N—CH$_3$, S, O |
| 13-16: A-D | 4-F | NH, N—CH$_3$, S, O |
| 17-20: A-D | 7-F, 2-CH$_3$ | NH, N—CH$_3$, S, O |
| 21-24: A-D | 7-F, 3-CH$_3$ | NH, N—CH$_3$, S, O |
| 25-28: A-D | 6-F, 2-CH$_3$ | NH, N—CH$_3$, S, O |
| 29-32: A-D | 6-F, 3-CH$_3$ | NH, N—CH$_3$, S, O |
| 33-36: A-D | 5-F, 2-CH$_3$ | NH, N—CH$_3$, S, O |
| 37-40: A-D | 5-F, 3-CH$_3$ | NH, N—CH$_3$, S, O |
| 41-44: A-D | 4-F, 2-CH$_3$ | NH, N—CH$_3$, S, O |
| 45-48: A-D | 4-F, 3-CH$_3$ | NH, N—CH$_3$, S, O |
| 49-52: A-D | 7-Cl | NH, N—CH$_3$, S, O |
| 53-56: A-D | 6-Cl | NH, N—CH$_3$, S, O |
| 57-60: A-D | 5-Cl | NH, N—CH$_3$, S, O |
| 61-64: A-D | 4-Cl | NH, N—CH$_3$, S, O |
| 65-68: A-D | 7-Cl, 2-CH$_3$ | NH, N—CH$_3$, S, O |
| 69-72: A-D | 7-Cl, 3-CH$_3$ | NH, N—CH$_3$, S, O |
| 73-76: A-D | 6-Cl, 2-CH$_3$ | NH, N—CH$_3$, S, O |
| 77-80: A-D | 6-Cl, 3-CH$_3$ | NH, N—CH$_3$, S, O |
| 81-84: A-D | 5-Cl, 2-CH$_3$ | NH, N—CH$_3$, S, O |
| 85-88: A-D | 5-Cl, 3-CH$_3$ | NH, N—CH$_3$, S, O |
| 89-92: A-D | 4-Cl, 2-CH$_3$ | NH, N—CH$_3$, S, O |
| 93-96: A-D | 4-Cl, 3-CH$_3$ | NH, N—CH$_3$, S, O |
| 97-100: A-D | 7-F, 6-F | NH, N—CH$_3$, S, O |
| 101-104: A-D | 7-F, 5-F | NH, N—CH$_3$, S, O |
| 105-108: A-D | 7-F, 4-F | NH, N—CH$_3$, S, O |
| 107-112: A-D | 6-F, 5-F | NH, N—CH$_3$, S, O |
| 113-116: A-D | 6-F, 4-F | NH, N—CH$_3$, S, O |
| 117-120: A-D | 5-F, 4-F | NH, N—CH$_3$, S, O |
| 121-124: A-D | 7-Cl, 6-Cl | NH, N—CH$_3$, S, O |
| 125-128: A-D | 7-Cl, 5-Cl | NH, N—CH$_3$, S, O |
| 129-132: A-D | 7-Cl, 4-Cl | NH, N—CH$_3$, S, O |
| 133-136: A-D | 6-Cl, 5-Cl | NH, N—CH$_3$, S, O |
| 137-140: A-D | 6-Cl, 4-Cl | NH, N—CH$_3$, S, O |
| 141-144: A-D | 5-Cl, 4-Cl | NH, N—CH$_3$, S, O |
| 145-148: A-D | 7-F, 6-Cl | NH, N—CH$_3$, S, O |
| 149-152: A-D | 7-F, 5-Cl | NH, N—CH$_3$, S, O |
| 153-156: A-D | 7-F, 4-Cl | NH, N—CH$_3$, S, O |
| 157-160: A-D | 6-F, 7-Cl | NH, N—CH$_3$, S, O |
| 161-164: A-D | 6-F, 5-Cl | NH, N—CH$_3$, S, O |
| 165-168: A-D | 6-F, 4-Cl | NH, N—CH$_3$, S, O |
| 169-172: A-D | 5-F, 7-Cl | NH, N—CH$_3$, S, O |
| 173-176: A-D | 5-F, 6-Cl | NH, N—CH$_3$, S, O |
| 177-180: A-D | 5-F, 4-Cl | NH, N—CH$_3$, S, O |
| 181-184: A-D | 4-F, 7-Cl | NH, N—CH$_3$, S, O |
| 185-188: A-D | 4-F, 6-Cl | NH, N—CH$_3$, S, O |
| 189-192: A-D | 4-F, 5-Cl | NH, N—CH$_3$, S, O |
| 193-196: A-D | 7-F, 6-F, 2-CH$_3$ | NH, N—CH$_3$, S, O |
| 197-200: A-D | 7-F, 5-F, 2-CH$_3$ | NH, N—CH$_3$, S, O |
| 201-204: A-D | 7-F, 4-F, 2-CH$_3$ | NH, N—CH$_3$, S, O |
| 205-208: A-D | 7-F, 6-F, 3-CH$_3$ | NH, N—CH$_3$, S, O |
| 209-212: A-D | 7-F, 5-F, 3-CH$_3$ | NH, N—CH$_3$, S, O |
| 213-216: A-D | 7-F, 4-F, 3-CH$_3$ | NH, N—CH$_3$, S, O |
| 217-220: A-D | 6-F, 5-F, 2-CH$_3$ | NH, N—CH$_3$, S, O |
| 221-224: A-D | 6-F, 4-F, 2-CH$_3$ | NH, N—CH$_3$, S, O |
| 225-228: A-D | 6-F, 5-F, 3-CH$_3$ | NH, N—CH$_3$, S, O |
| 229-232: A-D | 6-F, 4-F, 3-CH$_3$ | NH, N—CH$_3$, S, O |
| 233-236: A-D | 5-F, 4-F, 2-CH$_3$ | NH, N—CH$_3$, S, O |
| 237-240: A-D | 5-F, 4-F, 3-CH$_3$ | NH, N—CH$_3$, S, O |

| | | |
|---|---|---|
| 241-244: A-D | 6-Cl, 5-Cl, 2-CH₃ | NH, N—CH₃, S, O |
| 245-248: A-D | 6-Cl, 5-Cl, 3-CH₃ | NH, N—CH₃, S, O |
| 249-252: A-D | 6-Cl, 4-Cl, 2-CH₃ | NH, N—CH₃, S, O |
| 253-256: A-D | 6-Cl, 4-Cl, 3-CH₃ | NH, N—CH₃, S, O |
| 257-260: A-D | 6-(CH₃—S—) | NH, N—CH₃, S, O |
| 261-264: A-D | 6-(CH₃—S—), 2-CH₃ | NH, N—CH₃, S, O |
| 265-268: A-D | 6-(CH₃—S—), 3-CH₃ | NH, N—CH₃, S, O |
| 269-272: A-D | 6-(CH₃—S(O)—) | NH, N—CH₃, S, O |
| 273-276: A-D | 6-(CH₃—S(O)—), 2-CH₃ | NH, N—CH₃, S, O |
| 277-280: A-D | 6-(CH₃—S(O)—), 3-CH₃ | NH, N—CH₃, S, O |
| 281-284: A-D | 7-F, 6-(CH₃—S) | NH, N—CH₃, S, O |
| 285-288: A-D | 5-F, 6-(CH₃—S) | NH, N—CH₃, S, O |
| 289-292: A-D | 4-F, 6-(CH₃—S) | NH, N—CH₃, S, O |
| 293-296: A-D | 6-CF₃ | NH, N—CH₃, S, O |
| 297-300: A-D | 6-CF₃, 2-CH₃ | NH, N—CH₃, S, O |
| 301-304: A-D | 6-CF₃, 3-CH₃ | NH, N—CH₃, S, O |
| 305-308: A-D | 6-[—CH(CH₃)COOH] | NH, N—CH₃, S, O |
| 309-312: A-D | 6-[—CH(CH₃)COOH], 2-CH₃ | NH, N—CH₃, S, O |
| 313-316: A-D | 6-[—CH(CH₃)COOH], 3-CH₃ | NH, N—CH₃, S, O |
| 317-320: A-D | 6-CH₃ | NH, N—CH₃, S, O |
| 321-324: A-D | 6-CH₃, 2-CH₃ | NH, N—CH₃, S, O |
| 325-328: A-D | 6-CH₃, 3-CH₃ | NH, N—CH₃, S, O |

UNSUBSTITUTED PARENT STRUCTURES FOR COMPOUNDS 329-656:A-D

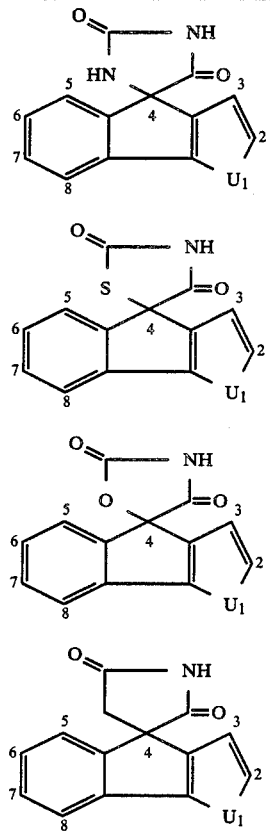

| Compound No. | Ring Substitution | U |
|---|---|---|
| 329-332:A-D | 7-F | NH,N—CH₃,S,O |
| 333-336:A-D | 6-F | NH,N—CH₃,S,O |
| 337-340:A-D | 5-F | NH,N—CH₃,S,O |
| 341-344:A-D | 8-F | NH,N—CH₃,S,O |
| 345-348:A-D | 7-F,2-CH₃ | NH,N—CH₃,S,O |
| 349-352:A-D | 7-F,3-CH₃ | NH,N—CH₃,S,O |
| 353-356:A-D | 6-F,2-CH₃ | NH,N—CH₃,S,O |
| 357-360:A-D | 6-F,3-CH₃ | NH,N—CH₃,S,O |
| 361-364:A-D | 5-F,2-CH₃ | NH,N—CH₃,S,O |
| 365-368:A-D | 5-F,3-CH₃ | NH,N—CH₃,S,O |
| 369-372:A-D | 8-F,2-CH₃ | NH,N—CH₃,S,O |
| 373-376:A-D | 8-F,3-CH₃ | NH,N—CH₃,S,O |
| 377-380:A-D | 7-Cl | NH,N—CH₃,S,O |
| 381-384:A-D | 6-Cl | NH,N—CH₃,S,O |
| 385-388:A-D | 5-Cl | NH,N—CH₃,S,O |
| 389-392:A-D | 8-Cl | NH,N—CH₃,S,O |
| 393-396:A-D | 7-Cl,2-CH₃ | NH,N—CH₃,S,O |
| 397-400:A-D | 7-Cl,3-CH₃ | NH,N—CH₃,S,O |
| 401-404:A-D | 6-Cl,2-CH₃ | NH,N—CH₃,S,O |
| 405-408:A-D | 6-Cl,3-CH₃ | NH,N—CH₃,S,O |
| 409-412:A-D | 5-Cl,2-CH₃ | NH,N—CH₃,S,O |
| 413-416:A-D | 5-Cl,3-CH₃ | NH,N—CH₃,S,O |
| 417-420:A-D | 8-Cl,2-CH₃ | NH,N—CH₃,S,O |
| 421-424:A-D | 8-Cl,3-CH₃ | NH,N—CH₃,S,O |
| 425-428:A-D | 7-F,6-F | NH,N—CH₃,S,O |
| 429-432:A-D | 7-F,5-F | NH,N—CH₃,S,O |
| 433-436:A-D | 7-F,8-F | NH,N—CH₃,S,O |
| 437-440:A-D | 6-F,5-F | NH,N—CH₃,S,O |
| 441-444:A-D | 6-F,8-F | NH,N—CH₃,S,O |
| 445-448:A-D | 5-F,8-F | NH,N—CH₃,S,O |
| 449-452:A-D | 7-Cl,6-Cl | NH,N—CH₃,S,O |
| 453-456:A-D | 7-Cl,5-Cl | NH,N—CH₃,S,O |
| 457-460:A-D | 7-Cl,8-Cl | NH,N—CH₃,S,O |
| 461-464:A-D | 6-Cl,5-Cl | NH,N—CH₃,S,O |
| 465-468:A-D | 6-Cl,8-Cl | NH,N—CH₃,S,O |
| 469-472:A-D | 5-Cl,8-Cl | NH,N—CH₃,S,O |
| 473-476:A-D | 7-F,6-Cl | NH,N—CH₃,S,O |
| 477-480:A-D | 7-F,5-Cl | NH,N—CH₃,S,O |
| 481-484:A-D | 7-F,8-Cl | NH,N—CH₃,S,O |
| 485-488:A-D | 6-F,7-Cl | NH,N—CH₃,S,O |
| 489-492:A-D | 6-F,5-Cl | NH,N—CH₃,S,O |
| 493-496:A-D | 6-F,8-Cl | NH,N—CH₃,S,O |
| 497-500:A-D | 5-F,7-Cl | NH,N—CH₃,S,O |
| 501-504:A-D | 5-F,6-Cl | NH,N—CH₃,S,O |
| 505-508:A-D | 5-F,8-Cl | NH,N—CH₃,S,O |
| 509-512:A-D | 8-F,7-Cl | NH,N—CH₃,S,O |
| 513-516:A-D | 8-F,6-Cl | NH,N—CH₃,S,O |
| 517-520:A-D | 8-F,5-Cl | NH,N—CH₃,S,O |
| 521-524:A-D | 7-F,6-F,2-CH₃ | NH,N—CH₃,S,O |
| 525-528:A-D | 7-F,5-F,2-CH₃ | NH,N—CH₃,S,O |
| 529-532:A-D | 7-F,8-F,2-CH₃ | NH,N—CH₃,S,O |
| 533-536:A-D | 7-F,6-F,3-CH₃ | NH,N—CH₃,S,O |
| 537-540:A-D | 7-F,5-F,3-CH₃ | NH,N—CH₃,S,O |
| 541-544:A-D | 7-F,8-F,3-CH₃ | NH,N—CH₃,S,O |
| 545-548:A-D | 6-F,5-F,2-CH₃ | NH,N—CH₃,S,O |
| 549-552:A-D | 6-F,8-F,2-CH₃ | NH,N—CH₃,S,O |
| 553-556:A-D | 6-F,5-F,3-CH₃ | NH,N—CH₃,S,O |
| 557-560:A-D | 6-F,8-F,3-CH₃ | NH,N—CH₃,S,O |
| 561-564:A-D | 5-F,8-F,2-CH₃ | NH,N—CH₃,S,O |
| 565-568:A-D | 5-F,8-F,3-CH₃ | NH,N—CH₃,S,O |
| 569-572:A-D | 6-Cl,5-Cl,2-CH₃ | NH,N—CH₃,S,O |
| 573-576:A-D | 6-Cl,5-Cl,3-CH₃ | NH,N—CH₃,S,O |
| 577-580:A-D | 6-Cl,8-Cl,2-CH₃ | NH,N—CH₃,S,O |
| 581-584:A-D | 6-Cl,8-Cl,3-CH₃ | NH,N—CH₃,S,O |
| 585-588:A-D | 6-(CH₃—S—) | NH,N—CH₃,S,O |
| 589-592:A-D | 6-(CH₃—S—),2-CH₃ | NH,N—CH₃,S,O |
| 593-596:A-D | 6-(CH₃—S—),3-CH₃ | NH,N—CH₃,S,O |
| 597-600:A-D | 6-(CH₃—S(O)—) | NH,N—CH₃,S,O |
| 601-604:A-D | 6-(CH₃—S(O)—),2-CH₃ | NH,N—CH₃,S,O |
| 605-608:A-D | 6-(CH₃—S(O)—),3-CH₃ | NH,N—CH₃,S,O |
| 609-612:A-D | 7-F,6-(CH₃—S) | NH,N—CH₃,S,O |
| 613-616:A-D | 5-F,6-(CH₃—S) | NH,N—CH₃,S,O |
| 617-620:A-D | 8-F,6-(CH₃—S) | NH,N—CH₃,S,O |
| 621-624:A-D | 6-CF₃ | NH,N—CH₃,S,O |
| 625-628:A-D | 6-CF₃,2-CH₃ | NH,N—CH₃,S,O |
| 629-632:A-D | 6-CF₃,3-CH₃ | NH,N—CH₃,S,O |
| 633-636:A-D | 6-[—CH(CH₃)COOH] | NH,N—CH₃,S,O |
| 637-640:A-D | 6-[—CH(CH₃)COOH],2-CH₃ | NH,N—CH₃,S,O |
| 641-644:A-D | 6-[—CH(CH₃)COOH],3-CH₃ | NH,N—CH₃,S,O |
| 645-648:A-D | 6-CH₃ | NH,N—CH₃,S,O |
| 649-652:A-D | 6-CH₃,2-CH₃ | NH,N—CH₃,S,O |
| 653-656:A-D | 6-CH₃,3-CH₃ | NH,N—CH₃,S,O |

UNSUBSTITUTED PARENT STRUCTURES FOR COMPOUNDS 657–706:A–D

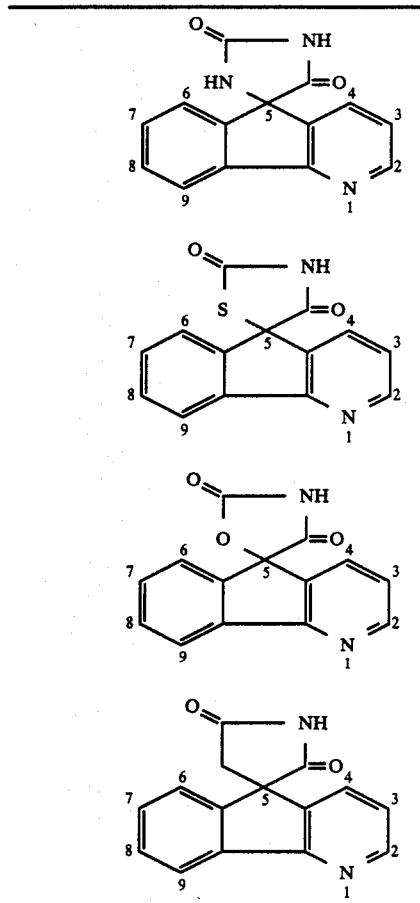

| Compound No. | Ring Substitution |
|---|---|
| 657: A–D | 6-F |
| 658: A–D | 7-F |
| 659: A–D | 8-F |
| 660: A–D | 9-F |
| 661: A–D | 3-F |
| 662: A–D | 6-F, 3-F |
| 663: A–D | 7-F, 3-F |
| 664: A–D | 8-F, 3-F |
| 665: A–D | 9-F, 3-F |
| 666: A–D | 6-Cl |
| 667: A–D | 7-Cl |
| 668: A–D | 8-Cl |
| 669: A–D | 9-Cl |
| 670: A–D | 6-Cl, 3-F |
| 671: A–D | 7-Cl, 3-F |
| 672: A–D | 8-Cl, 3-F |
| 673: A–D | 9-Cl, 3-F |
| 674: A–D | 6-F, 7-F |
| 675: A–D | 6-F, 8-F |
| 676: A–D | 6-F, 9-F |
| 677: A–D | 7-F, 8-F |
| 678: A–D | 7-F, 9-F |
| 679: A–D | 8-F, 9-F |
| 680: A–D | 3-F, 7-F, 8-F |
| 681: A–D | 7-($CH_3$—S) |
| 682: A–D | 7-($CH_3$—S(O)—) |
| 683: A–D | 7-[—CH($CH_3$)COOH] |
| 684: A–D | 7-[—CH($CH_3$)COOH], 3-$CH_3$ |
| 685: A–D | 7-[—CH($CH_3$)COOH], 2-$CH_3$ |
| 686: A–D | 7-[—CH($CH_3$)COOH], 4-$CH_3$ |
| 687: A–D | 6-[—CH($CH_3$)COOH] |
| 687: A–D | 6-[—CH($CH_3$)COOH], 3-$CH_3$ |
| 688: A–D | 6-[—CH($CH_3$)COOH], 2-$CH_3$ |
| 689: A–D | 6-[—CH($CH_3$)COOH], 4-$CH_3$ |
| 690: A–D | 7-$CH_3$ |
| 691: A–D | 7-($CH_3$—O) |
| 692: A–D | 7-$CF_3$ |
| 693: A–D | 7-COOH |
| 694: A–D | 7-$CONH_2$ |
| 695: A–D | 6-$CH_2$COOH |
| 696: A–D | 6-$CH_2$COOH, 3-$CH_3$ |
| 697: A–D | 6-$CH_2$COOH, 2-$CH_3$ |
| 698: A–D | 6-$CH_2$COOH, 4-$CH_3$ |
| 699: A–D | 6-COOH |
| 700: A–D | 6-$CH_2$—$NH_2$ |
| 701: A–D | 7-$CH_2$COOH |
| 702: A–D | 7-$CH_2$COOH, 3-$CH_3$ |
| 703: A–D | 7-$CH_2$COOH, 2-$CH_3$ |
| 704: A–D | 7-$CH_2$COOH, 4-$CH_3$ |
| 705: A–D | 7-COOH, 3-$CH_3$ |
| 706: A–D | 7-$CH_2$—$NH_2$ |

UNSUBSTITUTED PARENT STRUCTURES FOR COMPOUNDS 707–744:A–D

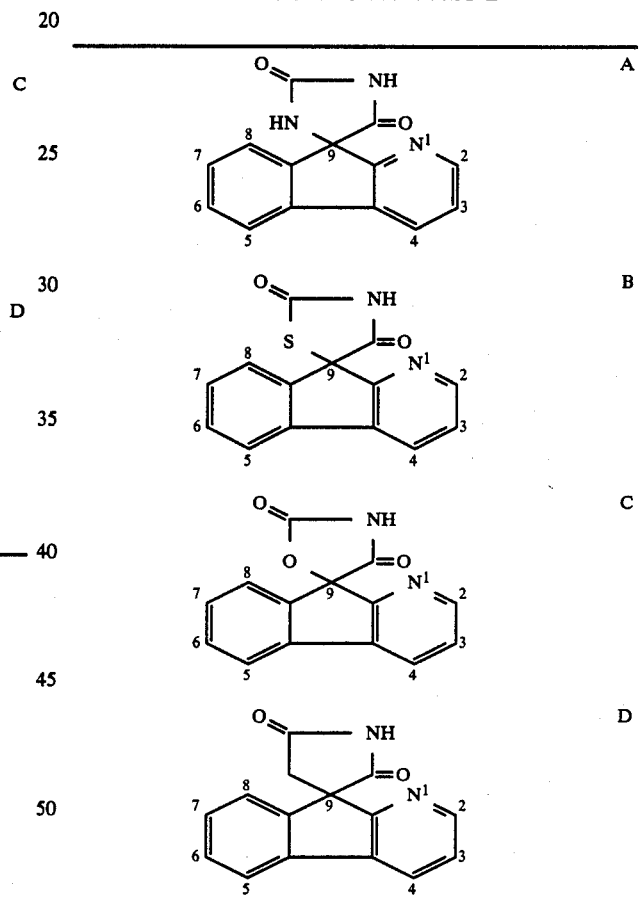

| Compound No. | Ring Substitution |
|---|---|
| 707: A–D | 8-F |
| 708: A–D | 7-F |
| 709: A–D | 6-F |
| 710: A–D | 5-F |
| 711: A–D | 7-Cl |
| 712: A–D | 5-F, 6-F |
| 713: A–D | 5-F, 7-F |
| 714: A–D | 5-F, 8-F |
| 715: A–D | 6-F, 7-F |
| 716: A–D | 6-F, 8-F |
| 717: A–D | 7-F, 8-F |
| 718: A–D | 7-($CH_3$—S) |
| 719: A–D | 7-($CH_3$—S(O)—) |
| 720: A–D | 7-COOH ... |
| 721: A–D | 7-$CH_3$ |

-continued

| | |
|---|---|
| 722:A-D | 7-CF$_3$ |
| 723:A-D | 7-[CH(CH$_3$)COOH] |
| 724:A-D | 7-[CH(CH$_3$)COOH],2-CH$_3$ |
| 725:A-D | 7-[CH(CH$_3$)COOH],3-CH$_3$ |
| 726:A-D | 7-[CH(CH$_3$)COOH],4-CH$_3$ |
| 727:A-D | 6-[CH(CH$_3$)COOH],2-CH$_3$ |
| 728:A-D | 6-[CH(CH$_3$)COOH],3-CH$_3$ |
| 729:A-D | 6-[CH(CH$_3$)COOH],4-CH$_3$ |
| 730:A-D | 6-[CH(CH$_3$)COOH],5-CH$_3$ |

UNSUBSTITUTED PARENT STRUCTURES FOR PARENT COMPOUNDS 731–766:A–D

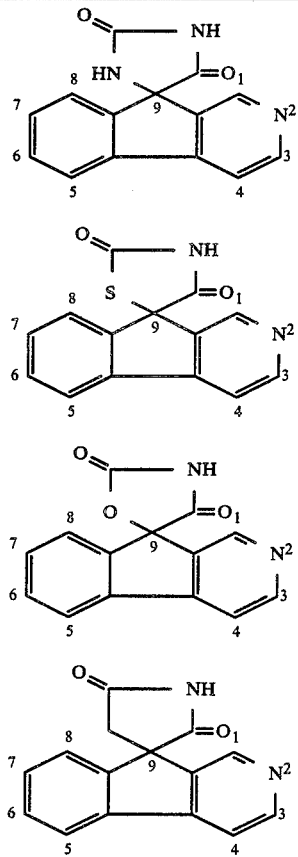

| Compound No. | Substitution Ring |
|---|---|
| 731:A-D | 8-F |
| 732:A-D | 7-F |
| 733:A-D | 6-F |
| 734:A-D | 5-F |
| 735:A-D | 7-Cl |
| 736:A-D | 5-F,6-F |
| 737:A-D | 5-F,7-F |
| 738:A-D | 5-F,8-F |
| 739:A-D | 6-F,7-F |
| 740:A-D | 6-F,8-F |
| 741:A-D | 7-F,8-F |
| 742:A-D | 7-(CH$_3$—S—) |
| 743:A-D | 7-(CH$_3$S(O)—) |
| 744:A-D | 7-COOH |
| 745:A-D | 7-CH$_3$ |
| 746:A-D | 7-CF$_3$ |
| 747:A-D | 7-[CH(CH$_3$)COOH] |
| 748:A-D | 7-[CH(CH$_3$)COOH],1-CH$_3$ |
| 749:A-D | 7-[CH(CH$_3$)COOH],3-CH$_3$ |
| 750:A-D | 7-[CH(CH$_3$)COOH],4-CH$_3$ |
| 751:A-D | 6-[CH(CH$_3$)COOH] |
| 752:A-D | 6-[CH(CH$_3$)COOH],1-CH$_3$ |
| 753:A-D | 6-[CH(CH$_3$)COOH],3-CH$_3$ |

-continued

| | |
|---|---|
| 754:A-D | 6-[CH(CH$_3$)COOH],4-CH$_3$ |
| 755:A-D | 7-CONH$_2$ |
| 756:A-D | 6-CONH$_2$ |
| 757:A-D | 7-CH$_2$COOH |
| 758:A-D | 7-CH$_2$COOH,1-CH$_3$ |
| 759:A-D | 7-CH$_2$COOH,3-CH$_3$ |
| 760:A-D | 7-CH$_2$COOH,4-CH$_3$ |
| 761:A-D | 6-CH$_2$COOH |
| 762:A-D | 6-CH$_2$COOH,1-CH$_3$ |
| 763:A-D | 6-CH$_2$COOH,3-CH$_3$ |
| 764:A-D | 6-CH$_2$COOH,4-CH$_3$ |
| 765:A-D | 6-COOH |
| 766:A-D | 6-Cl |

UNSUBSTITUTED PARENT STRUCTURES FOR COMPOUNDS 767–792:A–D

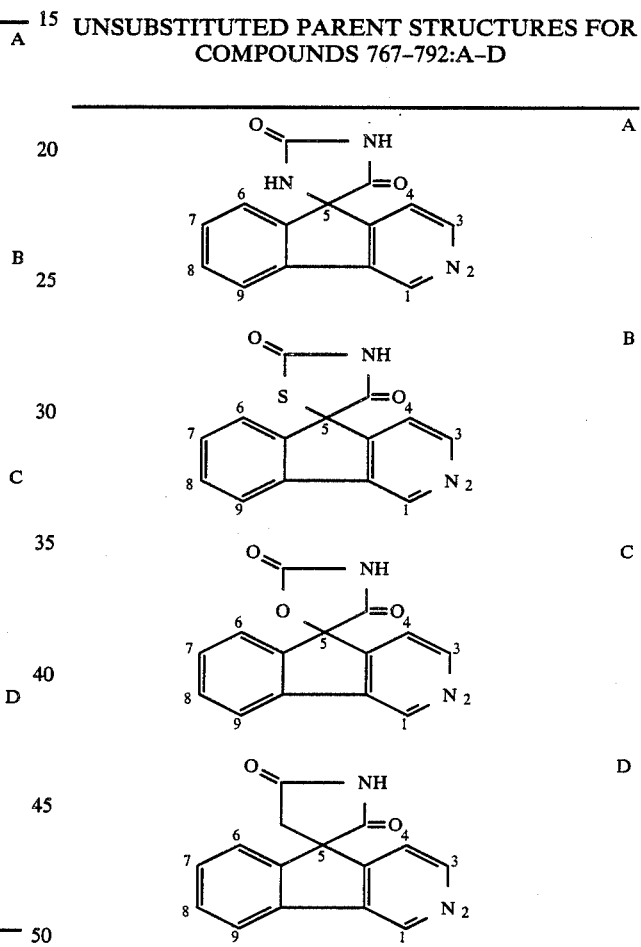

| Compound No. | Ring Substitution |
|---|---|
| 767:A-D | 9-F |
| 768:A-D | 8-F |
| 769:A-D | 7-F |
| 770:A-D | 6-F |
| 771:A-D | 7-Cl |
| 772:A-D | 8-Cl |
| 773:A-D | 7-(CH$_3$—S) |
| 774:A-D | 7-(CH$_3$—S(O)—) |
| 775:A-D | 7-[CH(CH$_3$)COOH] |
| 776:A-D | 6-[CH(CH$_3$)COOH] |
| 777:A-D | 7-COOH |
| 778:A-D | 7-CONH$_2$ |
| 779:A-D | 7-CF$_3$ |
| 780:A-D | 7-CH$_2$COOH |
| 781:A-D | 8-CH$_2$COOH |
| 782:A-D | 7-CH$_2$COOC$_2$H$_5$ |
| 783:A-D | 8-CH$_2$COOC$_2$H$_5$ |
| 784:A-D | 7-F,8-F |
| 785:A-D | 7-Cl,8-Cl |

| | -continued | |
|---|---|---|
| 786:A–D | 7-CH$_3$ | |
| 787:A–D | 7-CH$_2$—NH$_2$ | |
| 788:A–D | 7-NO$_2$ | |
| 789:A–D | 8-NO$_2$ | |
| 790:A–D | 7-CH$_2$—OH | |
| 791:A–D | 8-COOH | |
| 792:A–D | 8-CONH$_2$ | |

UNSUBSTITUTED PARENT STRUCTURES FOR COMPOUNDS 793–847:A–D

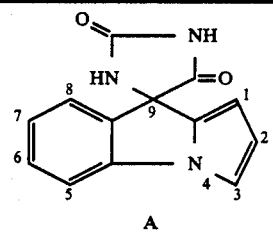

A

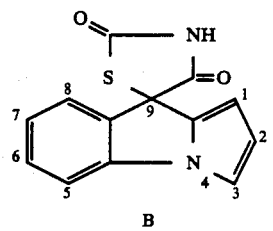

B

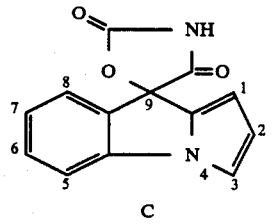

C

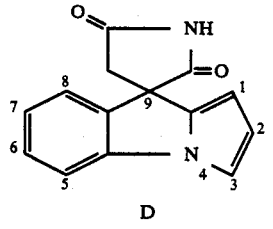

D

| Compound No. | Ring Substitution |
|---|---|
| 793:A–D | 8-F |
| 794:A–D | 7-F |
| 795:A–D | 6-F |
| 796:A–D | 5-F |
| 797:A–D | 8-F,1-CH$_3$ |
| 798:A–D | 8-F,2-CH$_3$ |
| 799:A–D | 8-F,3-CH$_3$ |
| 800:A–D | 7-F,1-CH$_3$ |
| 801:A–D | 7-F,2-CH$_3$ |
| 802:A–D | 7-F,3-CH$_3$ |
| 803:A–D | 6-F,1-CH$_3$ |
| 804:A–D | 6-F,2-CH$_3$ |
| 805:A–D | 6-F,3-CH$_3$ |
| 806:A–D | 5-F,1-CH$_3$ |
| 807:A–D | 5-F,2-CH$_3$ |
| 808:A–D | 5-F,3-CH$_3$ |
| 809:A–D | 7-Cl |
| 810:A–D | 7-Cl,1-CH$_3$ |
| 811:A–D | 7-Cl,2-CH$_3$ |
| 812:A–D | 7-Cl,3-CH$_3$ |
| 813:A–D | 7-(CH$_3$—S—) |
| 814:A–D | 7-(CH$_3$—S—),1-CH$_3$ |
| 815:A–D | 7-(CH$_3$—S—),2-CH$_3$ |
| 816:A–D | 7-(CH$_3$—S—),3-CH$_3$ |
| 817:A–D | 7-[CH$_3$—S(O)—] |
| 818:A–D | 7-[CH$_3$—S(O)—],1-CH$_3$ |
| 819:A–D | 7-[CH$_3$—S(O)—],2-CH$_3$ |
| 820:A–D | 7-[CH$_3$—S(O)—],3-CH$_3$ |
| 821:A–D | 6-F,7-F |
| 822:A–D | 7-Cl,6-F |
| 823:A–D | 7-[CH(CH$_3$)COOH] |
| 824:A–D | 7-[CH(CH$_3$)COOH],1-CH$_3$ |
| 825:A–D | 7-[CH(CH$_3$)COOH],2-CH$_3$ |
| 826:A–D | 7-[CH(CH$_3$)COOH],3-CH$_3$ |
| 827:A–D | 6-[CH(CH$_3$)COOH] |
| 828:A–D | 6-[CH(CH$_3$)COOH],1-CH$_3$ |
| 829:A–D | 6-[CH(CH$_3$)COOH],2-CH$_3$ |
| 830:A–D | 6-[CH(CH$_3$)COOH],3-CH$_3$ |
| 831:A–D | 6-CH$_2$COOH |
| 832:A–D | 6-CH$_2$COOH,1-CH$_3$ |
| 833:A–D | 6-CH$_2$COOH,2-CH$_3$ |
| 834:A–D | 6-CH$_2$COOH,3-CH$_3$ |
| 835:A–D | 7-CH$_2$COOH |
| 836:A–D | 7-CH$_2$COOH,1-CH$_3$ |
| 837:A–D | 7-CH$_2$COOH,2-CH$_3$ |
| 838:A–D | 7-CH$_2$COOH,3-CH$_3$ |
| 839:A–D | 6-Cl |
| 840:A–D | 6-COOH |
| 841:A–D | 6-CONH$_2$ |
| 842:A–D | 7-COOH |
| 843:A–D | 7-CONH$_2$ |
| 844:A–D | 6-OCH$_3$ |
| 845:A–D | 3-Cl |
| 846:A–D | 6-CH$_2$NH$_2$ |
| 847:A–D | 7-CH$_2$NH$_2$ |

UNSUBSTITUTED PARENT STRUCTURE FOR COMPOUNDS 848–876:A–D

A

B

C

-continued

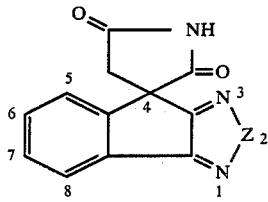

D

| Compound No. | Ring Substitution | Z |
|---|---|---|
| 848-849: A-D | 6-F | O,S |
| 850-851: A-D | 7-F | O,S |
| 852-853: A-D | 6-Cl | O,S |
| 854-855: A-D | 7-Cl | O,S |
| 856-857: A-D | 6-COOH | O,S |
| 858-859: A-D | 6-(CH$_3$—S) | O,S |
| 860-861: A-D | 6-[CH(CH$_3$)COOH] | O,S |
| 862-863: A-D | 7-[CH(CH$_3$)COOH] | O,S |
| 864-865: A-D | 6-CH$_2$COOH | O,S |
| 866-867: A-D | 7-CH$_2$COOH | O,S |
| 868-869: A-D | 7-COOH | O,S |
| 870-871: A-D | 6-CONH$_2$ | O,S |
| 872-873: A-D | 7-CONH$_2$ | O,S |
| 874-875: A-D | 6-F,7-F | O,S |

UNSUBSTITUTED PARENT STRUCTURE FOR COMPOUNDS 877-940:A-D

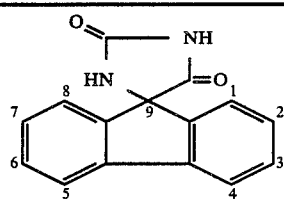 A

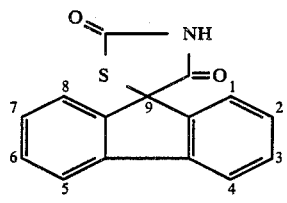 B

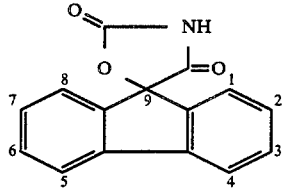 C

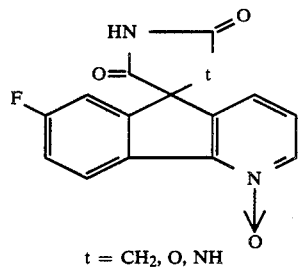 D

| Compound No. | Substitution Ring |
|---|---|
| 877:A-D | 1-F |
| 878:A-D | 2-F |
| 879:A-D | 3-F |
| 880-A-D | 4-F |
| 881:A-D | 1-F, 5-F |
| 882:A-D | 1-F, 6-F |
| 883:A-D | 1-F, 7-F |
| 884:A-D | 1-F, 8-F |
| 885:A-D | 2-F, 5-F |
| 886:A-D | 2-F, 6-F |
| 887:A-D | 2-F, 7-F |
| 888:A-D | 3-F, 5-F |
| 889:A-D | 3-F, 6-F |
| 890:A-D | 4-F, 5-F |
| 891:A-D | 2-Cl |
| 892:A-D | 2-Cl, 5-F |
| 893:A-D | 2-Cl, 6-F |
| 894:A-D | 2-Cl, 7-F |
| 895:A-D | 2-Cl, 8-F |
| 896:A-D | 2-F, 3-F, 7-F |
| 897:A-D | 2-F, 7-CH$_3$ |
| 898:A-D | 2-F, 7-(CH$_3$—S) |
| 899:A-D | 2-F, 7-(CH$_3$—S(O)) |
| 900-A-D | 2-F, 7-(CH$_3$—SO$_2$—) |
| 901:A-D | 2-Cl, 7-(CH$_3$—S) |
| 902:A-D | 2-Cl, 7-(CH$_3$—S(O)) |
| 903:A-D | 2-Cl, 7-(CH$_3$—SO$_2$—) |
| 904:A-D | 2-F, 7-(CH$_3$O—) |
| 905:A-D | 7-F, 2-COOH |
| 906:A-D | 6-F, 2-COOH |
| 907:A-D | 7-F, 3-COOH |
| 908:A-D | 6-F, 3-COOH |
| 909:A-D | 2-F, 2-[CH(CH$_3$)COOH] |
| 910:A-D | 2-Cl, 2-[CH(CH$_3$)COOH] |
| 911:A-D | 2-F, 2[CH(CH$_3$)COOH] |
| 912:A-D | 2-Cl, 2-[CH(CH$_3$)COOH] |
| 913:A-D | 2-(CH$_3$—S), 7-[CH(CH$_3$)COOH] |
| 914:A-D | 2-[CH$_3$—S(O)], 7-[CH(CH$_3$)COOH] |
| 915:A-D | 2-(CH$_3$—S), 6-[CH(CH$_3$)COOH] |
| 916:A-D | 2-[CH$_3$—S(O)], 6-[CH(CH$_3$)COOH] |
| 917:A-D | 7-F, 2-CONH$_2$ |
| 918:A-D | 7-Cl, 2-CONH$_2$ |
| 919:A-D | 7-F, 3-2, 7-(CH$_3$—S) |
| 920:A-D | 7-F, 3-2, 7-[CH$_3$S(O)] |
| 921:A-D | 2-F, 7-CF$_3$ |
| 922:A-D | 2-F, 7-OH |
| 923:A-D | 2-F, 6-OH |
| 924:A-D | 2-F, 5-OH |
| 925:A-D | 2-F, 7-(CH$_3$—O—) |
| 926:A-D | 2-COOH, 6-F, 7-F |
| 927:A-D | 3-COOH, 6-F, 7-F |
| 928:A-D | 2-(CH$_3$—S), 3-F |
| 929:A-D | 2-(CH$_3$—2), 4-F |
| 930:A-D | 2-F, 3-F, 7-(CH$_3$—S) |
| 931:A-D | 2-F, 3-F, 7-[CH$_3$—S(O)—] |
| 932:A-D | 2-F, 3-(CH$_3$—S—), 7-F |
| 933:A-D | 2-F, 3-[CH$_3$S(O)—], 7-F |
| 934:A-D | 1-F, 7-NO$_2$ |
| 935:A-D | 2-F, 7-NO$_2$ |
| 936:A-D | 3-F, 7-NO$_2$ |
| 937:A-D | 4-F, 7-NO$_2$ |
| 938:A-D | 2-[CH$_2$(CH$_3$)COOH] |
| 939:A-D | 2-CH$_2$COOH |
| 940:A-D | 2-CH$_2$COOH, 7-F |

EXAMPLE II

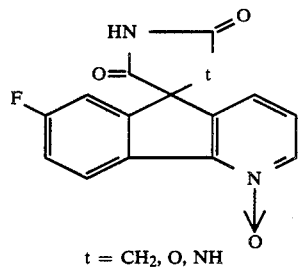

t = CH$_2$, O, NH

Preferred derivatives from Example XIX may be oxidized to yield the corresponding N-oxides. Similarly, other N-oxides are prepared from other spiro-tricyclic aromatic azine derivatives of the present invention.

Alternatively, an indenopyridine or indenopyridine ketone may be oxidized to the corresponding N-oxides prior to spiro derivatization.

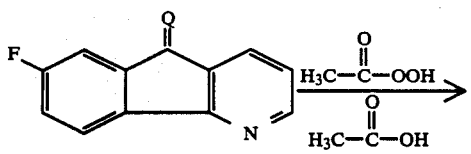

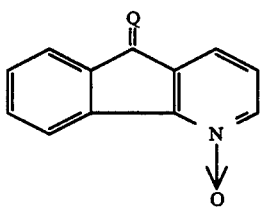

Q = H₂, O

EXAMPLE XXI

The sodium salt of spiro-(2-fluoro-9H-fluoren-9,5'-thiazolidine)-2',4'-dione, spiro-(6-fluoro-9H-pyrrolol[1,2-a]indol-9,4'-imidazolidine)-2,4'-dione, spiro-(7-fluoro-5H-indeno[1,2-b]pyridin-5,4'-imidazolidine)-2',5'-dione or any of their related spiro tricyclic congeners which are the subject of the present invention are prepared by dissolving any of said compounds in water containing an equivalent amount in moles of sodium hydroxide and then freeze-drying the mixture. In this way, the desired alkali metal salt of the spiro-hydantoin, spiro-thiazolidinedione, spiro-oxazolidinedione or spiro-succinimide can be prepared. In those cases where the aromatic substituents contain carboxylic acid moieties (e.g, isopropanoic acid substituent), one equivalent of base will yield the corresponding sodium carboxylate salt. In such cases as the afore-mentioned, two mole equivalents will yield the disodium salt. By this method, the desired alkali metal salt is obtained as an amorphous powder which is soluble in water.

In like manner, the potassium and lithium salts are analogously prepared, as are the alkali metal salts of all other spiro-tricycle compounds of this invention which are reported in Exmaples I-XVII and XIX, respectively.

EXAMPLE XXII

The calcium salt of spiro-(2-fluoro-9H-fluoren-9,5'-thiazolidine)-2',4'-dione is prepared by dissolving said compound in water containing an equivalent amount in moles of calcium hydroxide and then freeze-drying the mixture. The corresponding magnesium salt is also prepared in this manner, as are all other alkaline-earth metal salts not only of this particular compound, but also those spiro-tricyclic analogs previously described in Examples I-XVII and XIX, respectively.

Particularly preferred inhibitors are representatively indicated by the following list:
a. Spiro-(7-fluoro-4H-indeno[1,2-b]thiophen-4,4'-imidazolidine)-2',5'-dione;
b. Spiro-(2-fluoro-9H-fluoren-9,4'-imidazolidine)-2',5'-dione;
c. Spiro-(2-fluoro-9H-fluoren-9,3'-succinimide);
d. Spiro-(7-fluoro-5H-indeno[1,2-b]-pyridin-5,4'-imidazoline)-2',5'-dione;
e. Spiro-(7-chloro-5H-indeno[1,2-b]-[pyridin-5,4'-imidazoline)-2',5'-dione.
f. Spiro-(7-chloro-9H-pyrrolo[1,2-a]indol-9,4'-imidazolidine)-2',5'-dione.
g. Spiro-(2,7-difluoro-9H-fluoren-9,4'-imidazolidine)-2',5'-dione;
h. Spiro-(2,7-difluoro-9H-fluoren-9,3'-succinimide);
i. Spiro-(2,7-difluoro-9H-fluoren-9,5'-oxazolidine)-2',4'-dione.

The prefered route of administration for the compositions of the present invention is topically to the eye. The exact dosage regimen is left to the routine discretion of clinician taking into consideration the host's age, sex, weight, and his history accounting for or attributing to the ocular wound in question.

The most preferred compositions will have the chosen aldose reductase inhibitor present at a concentration ranging from 0.1% to 2.0 weight % in a vehicle selected from buffered water, aqeous buffered carbopol gel, perfluoroalkanes and/or perfluorotrialkylamines comprising a perfluoroalkane-type vehicle are fully disclosed and claimed in copending commonly assigned U.S. patent application Ser. No. 528,890 filed Sept. 2, 1983, which is incorporated herein by reference.

The following representative example illustrates suitable pharmaceutical compositions for topically delivery of the involved aldose reductase inhibitors for corneal wound healing.

EXAMPLE XXIII

Gel composition for topical, ocular administration:

| Ingredient | % by weight |
|---|---|
| 0.25% w/v of the compound Spiro-(7-chloro-5H—indeno [1,2-b]-pyridin-5,4'-imidazolidine) -2',5'-dione | 0.25% |
| Benzalkonium Chloride | 0.01% |
| Carboxypolymethylene (carbopol) | 1.0% |
| Hydrochloric Acid and/or | to adjust pH |
| Sodium hydroxide | to 5.0 to 5.5 |
| Purified Water (as gel) | q.s to 100% |

The following topical, ocular formulations are physically in the form of suspensions:
Suspension A

| Ingredient | % by wt. |
|---|---|
| Micronized Spiro-(2-fluoro-9H—fluoren-9,4'-imidazolidine)-2',5-dione | 1.0% |
| Perfluorotributylamine (as suspension) | 99.0% |

Suspension B

| Ingredient | % by wt. |
|---|---|
| Micronized spiro-(2,7-difluoro-9H—fluoren-9,3'-succinimide) | 1.0% |
| Hydroxymethylcellulose | 1.0% |
| Disodium edetate | 0.01% |
| Benzalkonium chloride | 0.01% |
| Sodium Acetate | 0.14% |
| Sodium Chloride | 0.52% |
| Hydrochloric Acid and/or Sodium Hydroxide | pH 4.5 to 5.5 |
| Purified Water | q.s. to 100% |

-continued

| Ingredient | % by wt. |
|---|---|
| (as suspension) | |

The following formulation is a selected representative of a solution for the ophthalmic indications of the present invention:

| Ingredient | % wt. |
|---|---|
| Spiro-(2-fluoro-5H—indeno[1,2-b]pyridin-5,4'-immidazolidine)-2',5'-dione | 0.10% |
| Carboxypolymethylene (carbopol) | 0.10% |
| Benzalkonium Chloride | 0.008% |
| Hydrochloric Acid and/or Sodium Hydroxide | to adjust pH 4.5 to 5.0 |
| Purified Water | q.s. 100% |

What is claimed is:

1. A method of promoting wound healing in a wounded host organ comprising applying to the wounded host organ a therapeutically effective wound healing amount of a pharmaceutical composition containing an aldose reductase inhibitor.

2. A method according to claim 1 wherein the host organ is the human eye.

3. A method according to claim 1 wherein the host is human and diabetic.

4. A method according to claim 1 wherein the aldose reductase inhibitor composition is applied topically to the host organ.

5. A method of promoting wound healing in a wounded host organ comprising topically applying to the wounded host organ a therapeutically effective wound healing amount of a pharmaceutical composition containing an aldose reductase inhibitor, selected from a compound of the formula:

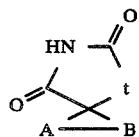

and the pharmaceutically acceptable salts thereof, wherein A and B are aromatic rings connected through two adjacent positions to a central five-membered ring, and are independently selected from the group consisting of:

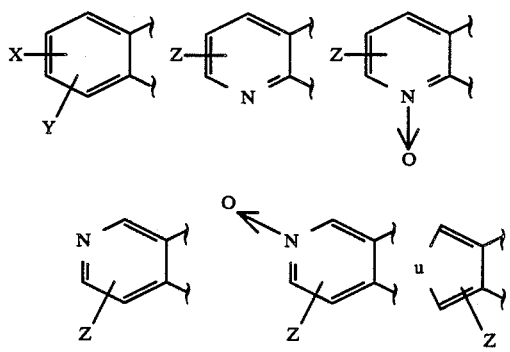

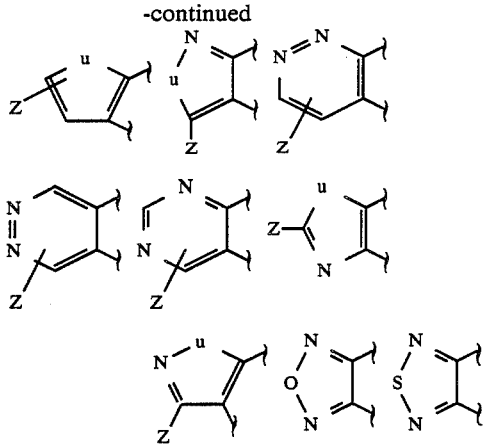

U is selected from the group consisting of O, S and $NR^1$;

X is selected from the group consisting of H, F, lower alkyl sulfide, and lower alkylsulfinyl;

Y is selected from H, —OH, —$OCOR^3$, F, Cl, lower alkyl, lower alkoxy, lower alkylsulfide, lower alkylsulfinyl, lower alkylsulfonyl, —$CF_3$, —S—$CF_3$, —$SO_2CF_3$, CO—N($R^1$)—$R^2$, lower alkyl alcohol, lower alkyl ether, nitro, lower alkyl sulfide, lower alkyl, lower alkylamine, lower alkyl esters, —COOH and lower alkyl esters, lower alkyl carboxylic acids and lower alkyl esters, and lower cycloalkyl; and $R^1$ and $R^2$ are selected from the group consisting of hydrogen and lower alkyl;

$R^3$ is lower alkyl;

Z is selected from the group consisting of hydrogen, lower alkyl, and halogen;

t is selected from the group consisting of $CHR^1$, NH, O, and S.

6. A method according to claim 5 wherein B is selected from:

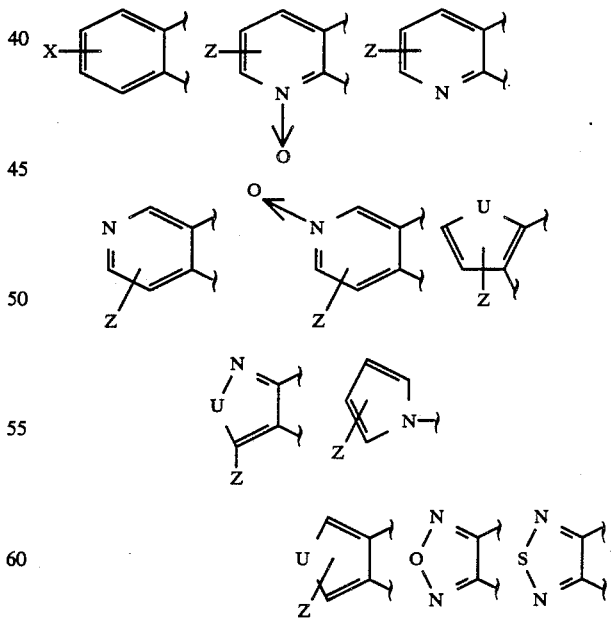

wherein X, U, and Z are as defined above.

7. A method according to claim 6 wherein the host organ is the human eye.

8. A method according to claim 6 wherein the host is human and diabetic.

* * * * *